(12) United States Patent
Michot et al.

(10) Patent No.: US 8,214,155 B2
(45) Date of Patent: Jul. 3, 2012

(54) METHODS FOR ANALYSIS OF MICRORNA

(75) Inventors: Bernard Michot, Tantene (FR); Olivier Delfour, Toulouse (FR); David Vilanova, Toulouse (FR); Jérôme Ciuti, Toulouse (FR); Florent Denoual, Toulouse (FR)

(73) Assignee: Cepheid, Sunnyvale, CA (US)

( * ) Notice: Subject to any disclaimer, the term of this patent is extended or adjusted under 35 U.S.C. 154(b) by 893 days.

(21) Appl. No.: 12/159,884

(22) PCT Filed: Jan. 4, 2007

(86) PCT No.: PCT/EP2007/050099
§ 371 (c)(1),
(2), (4) Date: Oct. 14, 2008

(87) PCT Pub. No.: WO2007/077249
PCT Pub. Date: Jul. 12, 2007

(65) Prior Publication Data
US 2010/0017140 A1  Jan. 21, 2010

(30) Foreign Application Priority Data
Jan. 4, 2006 (FR) .................................. 06 00044

(51) Int. Cl.
*G06F 7/00* (2006.01)

(52) U.S. Cl. .............. 702/19; 702/20; 703/11; 707/700; 435/6.1; 536/24.1

(58) Field of Classification Search ........................ None
See application file for complete search history.

(56) References Cited

OTHER PUBLICATIONS

Enright, Anton J. et al.; "MicroRNA targets in *Drosophila*"; 2003, Genome Biology, vol. 5, No. 1, pp. R1.1-R.1.14.
Ito, Mikito et al.; "Functional analysis of 1440 *Escherichia coli* genes using the combination of knock-out library and phenotype microarrays"; 2005; *Metabolic Engineering*, vol. 7, pp. 318-327.
Lewis, Benjamin P. et al.; "Prediction of Mammalian MicroRNA Targets"; 2003, *Cell*, vol. 115, pp. 787-798.

*Primary Examiner* — Mary Zeman
(74) *Attorney, Agent, or Firm* — Kilpatrick Townsend & Stockton LLP; David B. Raczkowski

(57) ABSTRACT

The present invention concerns a method for identifying the functionality of each member of a family of nucleic acids interact with the first family. Nucleic acids from the first family are put into functionally related clusters that share biological information obtained from the second family. The invention also relates to the refinement and accurate prediction of interactions between the first family and the second family of nucleic acids. The invention also applies to the use of such functional information to identify targets and mechanisms for therapeutic applications.

37 Claims, 16 Drawing Sheets

| microRNA | TRS | Protein | Functional annotation (GO) |
|---|---|---|---|
| Mir-1 | TRS 1 | Prot. A | Function A, B, C ... |
| Mir-1 | TRS 2 | Prot. B | Function A, C, D ... |
| Mir-1 | TRS 6 | Prot. D | Function A, C, E ... |
| Mir-2 | TRS 3 | Prot. B | Function A, C, D ... |
| Mir-2 | TRS 4 | Prot. C | Function B, C, E ... |
| Mir-3 | TRS 5 | Prot. C | Function B, C, E ... |
| Mir-3 | TRS 7 | Prot. E | Function A, B, D ... |

FIG. 7

|       | Gene a | Gene b | Gene c | Gene d | Gene e | ... |
|-------|--------|--------|--------|--------|--------|-----|
| miR-1 | 1      | 0      | 1      | 1      | 0      |     |
| miR-2 | 1      | 1      | 1      | 0      | 1      |     |
| miR-3 | 1      | 0      | 1      | 1      | 0      |     |

FIG. 9A

|       | GO a $\{Gene\ a, Gene\ c\}$ | GO b $\{Gene\ a, Gene\ b\}$ | GO c $\{Gene\ i, Gene\ a, Gene\ c\}$ | GO d $\{Gene\ h, Gene\ d, Gene\ b\}$ | GO e $\{Gene\ e, Gene\ f\}$ | ... |
|-------|------|------|------|------|------|-----|
| miR-1 | 1    | 0    | 1    | 1    | 0    |     |
| miR-2 | 1    | 0    | 1    | 0    | 0    |     |
| miR-3 | 1    | 0    | 1    | 1    | 0    |     |

| TABLE 1 | |
|---|---|
| Identification "functional families" | microRNAs present in the family |
| F1 | mir-365-1, mir365-2 |
| F2 | mir-219-1, mir-219-2 |
| F3 | mir-141, (mir-200a, mir-200b, mir-200c), mir-488 |
| F5 | (mir-193, mir-193b), mir-299 |
| F6 | (mir-23a, mir-23b) |
| F7 | (mir-181a, mir-181b-1, mir-181b-2, mir-181c, mir-181-d) |
| F8 | (mir-101-1, mir-101-2), mir-144 |
| F10 | mir-190, mir-384 |
| F12 | mir-34a, mir-34c, mir-210, mir-449 |
| F13 | mir-18, mir-20, mir20b, mir-106a |
| F14 | mir-150, mir-153-2, mir-331 |
| F17 | mir-191, mir-342 |
| F18 | mir-137, mir-192, mir-377, mir-504 |
| F19 | (mir-99a, mir-99b, mir-100) |
| F21 | (mir-329-2, mir-329-2-bis) |
| F22 | (mir-19a, mir-19b-2),mir-218-1, mir-218-2), mir-22, mir-301, mir-381 |
| F23 | (mir-30a, mir-30e), mir- 199b, mir-432 |
| F24 | (mir-148a, mir-148b) |
| F25 | mir-383, mir-409 |
| F26 | (mir- 196a-1, mir-196a-2) |
| F27 | Let-7b, Let-7c, Let-7i |
| F28 | Let-7f-1, Let-7f-2, Let-7a-3, Let-7a-2, Let-7a-1, Let-7g, Let-7c |
| F30 | mir-98, mir-142, let-7d |
| F31 | mir-143, mir-183 |
| F34 | (mir-10a, mir-10b) |
| F36 | (mir-125a, mir-125b-1, mir-125b-2) |
| F38 | (mir-30b, mir-30c-1, mir-30c-2, mir-30d) |
| F39 | (mir-128a, mir-128b) |
| F40 | mir-21, mir-33, mir-106b, mir-346 |
| F41 | (mir-1-1, mir-1-2), (mir-130a, mir-130b), mir-206 |
| F42 | (mir-146, mir-146b), mir-217, mir-345, mir-412 |
| F43 | (mir-376a, rnir-376b, mir-376b-bis), mir-368 |
| F44 | mir-188, mir-362 |
| F45 | (mir-26a-1, mir-26a-2, mir-26b), mir-370 |
| F46 | mir-296, mir-337 |
| F47 | (mir-135a-1, mir-135a-2, mir-135b), mir-134 |
| F48 | (mir-24-1, mir-24-2), mir-7-1 |
| F49 | (mir-27-a, mir-27-b), (mir-103-1, mir-103-2), mir-107 |
| F50 | mir-221, mir-222, mir-452 |
| F51 | mir-15a, mir-324, mir-431, mir-497 |
| F52 | (mir-129-1, mir-129-2), mir-182, mir-491, (mir-9-1, mir-9-2, mir-9-3), mir-453 |
| F55 | mir-18b, mir-93, (mir-302a, mir-302b) |
| F56 | mir-31, mir-185, mir-302c, mir-302d, mir-320, mir-425 |
| F58 | mir-34b, mir-154, mir-155, mir-184, mir-382 |
| F61 | (mir-29a, mir-29b-1, mir-29b-2, mir-29c) |
| F62 | mir-132, mir-212 |
| F63 | mir- 17, mir-122a, mir-140, (mir-511-1, mir-511-2) |
| F65 | mir-202, mir-506 |
| F66 | mir-92-2, mir-367 |
| F67 | mir-145, mir-149, mir-152, mir-502 |
| F68 | (mir-133a-1, mir-133b), mir-363, mir-448 |
| F72 | (mir-124a-1, mir-124a-2, mir-124a-3), mir-136, mir-380 |
| F73 | (mir-199a-1, mir-199a-2), mir-213, mir-214, mir-361, mir-493 |
| F75 | (mir-450, mir-450-2), mir-208, mir-499 |
| F87 | mir-204, mir-223, mir-326 |
| F88 | mir-96, mir-323, mir-379 |
| F89 | (mir-16-1, mir-16-2), mir15b, mir-424, mir-503 |

TABLE 2

| Identification orphan "functional families" | microRNA |
| --- | --- |
| F4 | mir-335 |
| F9 | mir-138-2 |
| F11 | mir-500 |
| F15 | mir-374 |
| F16 | mir-369 |
| F20 | mir-496 |
| F29 | mir-410 |
| F32 | mir-338 |
| F33 | mir-105-2 |
| F35 | mir-451 |
| F37 | mir-495 |
| F53 | mir-330 |
| F54 | mir-375 |
| F57 | mir-423 |
| F59 | mir-139 |
| F60 | mir-203 |
| F64 | mir-25 |
| F69 | mir-505 |
| F70 | mir-194-2 |
| F71 | mir-216 |
| F74 | mir-494 |
| F76 | mir-224 |
| F77 | mir-490 |
| F78 | mir-186 |
| F79 | mir-220 |
| F80 | mir-429 |
| F81 | mir-32 |
| F82 | mir-187 |
| F83 | mir-492 |
| F84 | mir-205 |
| F85 | mir-127 |
| F86 | mir-195 |

FIG. 13

TABLE 3

| Identification "functional groups" | "Functional families" grouped together |
|---|---|
| G1 | Families 3 and 5 |
| G2 | Families 7 and 8 |
| G3 | Families 4 and 12 |
| G4 | Families 29 and 13 |
| G5 | Families 79 and 18 |
| G6 | Families 27 and 28 (Let-7) |
| G7 | Families 80 and 38 |
| G8 | Families 40 and 87 |
| G9 | Families 41 and 88 |
| G10 | Families 82 and 42 |
| G11 | Families 86 and 89 |
| G12 | Families 54 and 52 |
| G13 | Families 55 and 56 |
| G14 | Families 53 and 58 |
| G15 | Families 25 and 63 |
| G16 | Families 84 and 67 |
| G17 | Families 72 and 73 |
| G18 | Families 85 and 75 |

FIG. 14

TABLE 4

| Identification of the "functional families" | Name of the paralogous microRNAs | % similarity |
|---|---|---|
| F1 | mir-365-1, mir365-2 | 100 |
| F2 | mir-219-1, mir-219-2 | 100 |
| F3 | mir-200a, mir-200b, mir-200c | 78.3 |
| F5 | mir-193, mir-193b | 70.8 |
| F6 | mir-23a, mir-23b | 95.5 |
| F7 | mir-181a, mir-181b-1, mir-181b-2, mir-181c, mir-181-d | 80 |
| F8 | mir-101-1, mir-101-2 | 100 |
| F13 | mir-20, mir-20b | 91.3 |
| F19 | mir-99a, mir-99b, mir-100 | 81.8 |
| F21 | mir-329-2, mir-329-2-bis | 100 |
| F22 | mir-19a, mir-19b-2 | 95.6 |
| F22 | mir-218-1, mir-218-2 | 100 |
| F24 | mir-148a, mir-148b | 91.3 |
| F26 | mir-196a-1, mir-196a-2 | 100 |
| F34 | mir-10a, mir-10b | 91.3 |
| F36 | mir-125a, mir-125b-1, mir-125b-2 | 82.6 |
| F39 | mir-128a, mir-128b | 95.5 |
| F41 | mir-1-1, mir-1-2 | 100 |
| F41 | mir-130a, mir-130b | 91 |
| F42 | mir-146, mir-146b | 86.4 |
| F43 | mir-376a, mir-376b, mir-376b-bis | 95.5 |
| F45 | mir-26a-1, mir-26a-2, mir-26b | 85.7 |
| F47 | mir-135a-1, mir-135a-2, mir-135b | 91.3 |
| F48 | mir-24-1, mir-24-2 | 100 |
| F49 | mir-27-a, mir-27-b | 95.2 |
| F49 | mir-103-1, mir-103-2 | 100 |
| F52 | mir-129-1, mir-129-2 | 100 |
| F52 | mir-9-1, mir-9-2, mir-9-3 | 100 |
| F61 | mir-29a, mir-29b-1, mir-29b-2, mir-29c | 82.6 |
| F63 | mir-511-1, mir-511-2 | 100 |
| F68 | mir-133a-1, mir-133b | 91 |
| F72 | mir-124a-1, mir-124a-2, mir-124a-3 | 100 |
| F75 | mir-450, mir-450-2 | 100 |
| F89 | mir-16-1, mir-16-2 | 100 |

FIG. 15

TABLE 5

| Identification functional families | microRNAs | Identification functional groups |
|---|---|---|
| | mir-15a, mir-15b | Similarity: 81.8 % |
| F51 | mir-15a | --- |
| F89 | mir15b | G11 |
| | mir-18, mir-18b | Similarity: 95.4% |
| F13 | mir-18 | G4 |
| F55 | mir-18b | G13 |
| | mir-34a, mir-34b, mir-34c | Similarity: 79.2 % |
| F12 | mir-34a, mir-34c | G3 |
| F58 | mir-34b | G14 |
| | mir-106a, mir-106b | Similarity: 75 % |
| F13 | mir-106a | G4 |
| F40 | mir-106b | G8 |
| | paralogous mir-30 | Similarity: 63.6 % |
| F23 | mir-30a, mir-30e | --- |
| F38 | mir-30b, mir-30c-1, mir-30c-2, mir-30d | G7 |
| | mir-199a-1, mir-199a-2, mir-199b | Similarity: 91.3 % |
| F23 | mir-199b | --- |
| F73 | mir-199a-1, mir-199a-2 | G17 |
| | paralogous mir-302 | Similarity: 86.9 % |
| F55 | mir-302a, mir-302b | G13 |
| F56 | mir-302c, mir-302d | G13 |
| | paralogous Let-7 | Similarity: 77.3 % |
| F27 | Let-7b, Let-7c, Let-7i | G6 |
| F28 | Let-7f-1, Let-7f-2, Let-7a-3, Let-7a-2, Let-7a-1, Let-7g, Let-7e | G6 |
| F30 | let-7d | --- |

FIG. 16

METHODS FOR ANALYSIS OF MICRORNA

CROSS-REFERENCES TO RELATED APPLICATIONS

This application claims the benefit of French Application No. 0600044, filed Jan. 4, 2006, the entire contents of which are incorporated herein by reference.

FIELD OF THE INVENTION

This invention generally relates to bioinformatics, and more particularly to the identification of the biological function and/or more reliable interaction targets of a first family of nucleic acids, such as microRNA, using functional clustering and distance matrices.

BACKGROUND OF THE INVENTION

MicroRNAs (miRNAs) constitute a vast family of very small molecules. In humans, their number is currently estimated as more than 1000 and their size is typically between 17 and 25 nucleotides. The majority of microRNAs are subjected to two types of regulations: firstly, a temporal regulation and, secondly, a spatial regulation. The temporal regulation depends on cell, tissue and organism growth, differentiation and development steps. The spatial regulation reflects, for its part, the fact that microRNAs are specifically expressed in a genus, a tissue type or a cell type (Reinhart, 2000). The spatial regulation can be determined by an antisense capacity of the microRNA.

The antisense capacity allows the miRNA to exert one or more specific biological phenomena by virtue of more or less extended base pairings (complementarity) with predetermined regions of respective target molecules. These target molecules and these regions constitute what is commonly referred to as target messenger RNAs (mRNAs) and target recognition sequences (TRSs), respectively. Depending, in particular, on the location and the type of complementarity (complete or partial), microRNAs will lead to either a repression of the translation of the mRNAs, or a destruction of the latter. Thus, microRNAs can control the expression of proteins produced from messenger RNAs (mRNAs).

As a result, miRNA have the ability to determine how, when and where genes must be expressed and also the ability to coordinate the interactions between these genes. Even more generally, microRNAs orchestrate numerous aspects of cell and organism development and function, and play key roles in the regulation of fundamental cell mechanisms (Brennecke et al., 2005; Chen et al., 2004; Esau et al., 2004; Yekta S. et al., 2004). Unfortunately, in animals in general and humans in particular, it is not known, except for a few rare exceptions, which biological phenomenon (functions) are associated with which microRNA. Therefore, an important step today is identifying which microRNAs control respectively one or more specific biological phenomena and how the control is performed.

However, it has proven difficult to associate a specific biological phenomenon with a particular microRNA. One of the reasons lies in the few structural constraints that are exerted on the microRNA-mRNA duplexes. For example, in animals, unlike plants, these duplexes contain numerous mismatches, internal loops, and Wobble-type pairing (G:U). In addition, the number of consecutive pairings is very short (typically between 8 and 10 nucleotides located at the 5' end of the microRNA (Lai et al., 2002)). Due to this weak interaction (including bulges and loops) between miRNA and its target (mRNA), thousands of possibilities can be predicted. Thus, the resulting list contains a majority of off-targets (i.e. background noise or false positives).

Identification of the targets, i.e. of the messenger RNAs, of the microRNAs by means of a simple molecular biology approach is therefore extremely difficult, or even impossible at this time. In an attempt to reply to such a problem, bioinformatics tools known, for example, under the following names: "Pictar" (Krek et al., 2005); "DIANA-microT" (Kiriakidou et al., 2004); "TargetScan" (Lewis et al., 2003); "(MiRanda" Enright et al., 2003), have been developed. These tools create binary relationships between microRNAs and their respective potential target recognition sequence(s). In other words, they associate an appropriate potential target recognition sequence list with each microRNA taken individually and, in the end, provide a gross list of these associations.

Although these tools have been useful in many ways, the existing tools have drawbacks. One drawback is that they result in a number of potential target recognition sequences for each microRNA that is much too great, which limits the exploitation of the results. Specifically, it is difficult to differentiate, in these large lists, the real (true) biological targets from the background noise.

Moreover, there is a great disparity in results between these tools for the same microRNA. For example, for the miR-15 microRNA, the "Pictar" tool provides a list of 746 possible targets, whereas, in "miRBase", "TargetScan" and "MiRanda", the list goes to 3918, 596 and 3456 potential target recognition sequences, respectively. By way of another example, for the miR-19 microRNA, the number of potential target recognition sequences provided is, respectively, 677, 5528, 527 and 1453. This further illustrates the abovementioned exploitation limits.

Therefore, it is desirable for improved methods of determining the biological functions associated with microRNA as well as their true target sequences. Additionally, it is desirable that these methods be transferable to other families of nucleic acids that are similarly situated.

BRIEF SUMMARY OF THE INVENTION

This invention provides methods, systems, and apparatus for identifying the biological functions of a first family of nucleic acids (such as miRNA) and the mechanisms by which the biological functions are achieved, e.g., the true target sequences of the nucleic acids, based on biological data of their target nucleic acids. In one aspect, the family nucleic acids are analyzed by reference to a second family of target nucleic acids. The members of the first family are functionally characterized through the functional characteristics of their target nucleic acids. Clusters are made of the nucleic acids of the first family using biological data associated with specific target nucleic acids that can interact with the first family. To each of these clusters, possible functions are associated from certain members of the second family.

In addition, interactions with the target family are predicted. Thus, the clustering method also can be used to decrease the background noise (false positives) in the predicted interactions. By comparison with the prior art, embodiments make it possible to identify approximately 20 to 50 potential targets per microRNA, against several hundred or several thousand. Such a reduction makes the results entirely exploitable, e.g., through biological experimentation. The partners of protein expression regulatory mechanisms, and/or to complete biological networks and/or molecular event cascades and/or metabolic pathways may be identified.

Accordingly, in a first aspect, the invention provides a method of analyzing a set of first nucleic acids that can interact with at least one target portion of respective target nucleic acids to identify at least one cluster of the first nucleic acids that potentially cooperate with one another so as to affect one or more biological functions. In some embodiments, the methods include an analysis of each first nucleic acid and target nucleic acid pair to determine whether a first nucleic acid interacts with a target nucleic acid. This interaction may be based on complementarily between the nucleic acids. Also, the first nucleic acids and the target nucleic acids may be from different nucleic acid families.

For each determined interaction, one or more biological data that are linked to the target nucleic acid of that interaction are identified. The biological data may be the name of a target nucleic acid, a corresponding gene, functional annotations, or other characteristic data of the target nucleic acids. For each of the first nucleic acids, at least a portion of the biological data linked to the target nucleic acids with which that first nucleic acid interacts may be associated with that first nucleic acid.

A correlation matrix is created that indicates whether each of the identified biological data is associated with each of the first nucleic acids. A distance matrix is created by defining a distance between each pair of the first nucleic acids based on the correlation matrix. The first nucleic acids are clustered based on the distance matrix. The clustering may include creating a dendrogram or similar structure. The clustering may include using a weighted pair group method with arithmetic mean (WPGMA).

A set of biological functions may then be linked with the biological data associated with the first nucleic acids of the cluster. At least a portion of the biological functions are assigned to the first nucleic acids of a cluster. In one embodiment, the biological functions define with which target nucleic acids do the first nucleic acids of the cluster interact. In another embodiment, the biological data associated with the first nucleic acids of the cluster includes the set of biological functions. In yet another embodiment, the portion of the biological functions assigned to the first nucleic acids of the cluster corresponds to biological data that is shared by the first nucleic acids of the cluster. The target nucleic acids linked with the shared biological data may be identified as true targets of the first nucleic acids of the cluster.

In another embodiment, the first nucleic acids and the target nucleic acids are each from an RNA nucleic acid family. For example, the first nucleic acids may be microRNA (or other non-coding RNA) and the target nucleic acids may be messenger RNA. The target portions may be in a 3'UTR region of the messenger RNA.

In one embodiment, clustering the first nucleic acids includes calculating a first amount of biological data shared by a set of the first nucleic acids and creating a cluster of the first nucleic acids if the first amount is at least a predetermined amount. The predetermined amount may be a percentage based on a total number of biological data associated with the first nucleic acids of the cluster. In another embodiment, clustering the first nucleic acids includes identifying a depth related to a set of first nucleic acids and creating a cluster if the depth is below a predetermined value.

In some embodiments, a "0" value of a correlation matrix element indicates that specific biological data is not associated with a specific first nucleic acid, and a "1" value of the correlation matrix element indicates that the specific biological data is associated with the specific first nucleic acid. In another embodiment, a correlation matrix element indicates a degree that biological data is associated with each of the first nucleic acids.

In one embodiment, defining a distance includes taking a difference between corresponding correlation matrix elements for each of the biological data of the first nucleic acids of the pair. Defining a distance may further include summing a function of each of the differences. In another embodiment, the distance is based on a similarity distance calculation.

In one embodiment, a complete list of all of the biological data linked to the target nucleic acid of the interactions is created. For each first nucleic acid, a specific list of the biological data linked to the target nucleic acid with which that first nucleic acid interacts is also created. Associating with a first nucleic acid at least a portion of the biological data linked to the target nucleic acids with which that first nucleic acid interacts may then include comparing the specific list for the first nucleic acid to the complete list to determine the portion of the biological data to associate with the first nucleic acid. The complete list and the specific lists of the biological data linked to the target nucleic acid with which that first nucleic acid interacts may be relational trees. Comparing may include using a statistical method to calculate a significance value of each of the biological data in the list, and only biological data having a significance value within a predetermined range may be included in the portion of the biological data associated with the first nucleic acid. The statistical method may be based on a hypergeometric distribution.

In another embodiment, determining whether that first nucleic acid respectively interacts with each of the target nucleic acids may include identifying in the target portion of the target nucleic acid: a first zone in which no break in complementarity with the first molecule (M) is permitted; and adjacent to the first zone, a second zone in which one or more breaks in complementarity with the first nucleic acid are permitted. An energy of interaction of the first and second zones may then be determined. In one aspect, the first zone in the target portion corresponds to a spatially extended nucleus (Nu).

In another aspect, the invention provides a computer program product comprising a computer readable medium encoded with program code for controlling operation of a computer system to analyze a set of first nucleic acids that can interact with at least one target portion of respective target nucleic acids to identify at least one cluster of the first nucleic acids that potentially cooperate with one another so as to affect one or more biological functions. The program code may include any code for implementing any method described herein.

In another aspect, the invention provides a method of analyzing a set of first nucleic acids that can interact with at least one target portion of respective target nucleic acids to identify which target nucleic acids are regulated by which of the first nucleic acids. In some embodiments, the methods include determining, for each of the first nucleic acids, whether that first nucleic acid respectively interacts with each of the target nucleic acids. Also, for each first nucleic acid, a respective set of target nucleic acids that interact with that first nucleic acid is identified. An intersection of the respective sets corresponding to at least two of the first nucleic acids is calculated. A determination is made as to whether a number of target nucleic acids in the intersection is larger than a predetermined amount. This determination may include for each of the at least two of the first nucleic acids: calculating a percentage by dividing the number of target nucleic acids in the intersection by a total number of target nucleic acids in the respective set of target nucleic acids that interact with that first nucleic acid, and comparing the percentage to the predetermined amount.

A cluster of the at least two of the first nucleic acids is created when the number of target nucleic acids in the intersection is larger than the predetermined amount. The target nucleic acids contained within the intersection are identified as true targets of the first nucleic acids of the cluster. The predetermined amount may be a percentage, such as 25%. A percentage may be calculated for each first nucleic acid of the cluster and may be separately based on the total number of interacting targets for that first nucleic acid.

DEFINITIONS

The term "biological function" as used herein refers to a role, a control by one or more molecules of a biological phenomenon, It will be noted, in this regard, that, in this text, a function (F) or, in an equivalent manner, a biological phenomenon refers in particular to a biological function and/or a metabolic pathway and/or a molecular event or a cascade of molecular events (processes). Also a more refined choice for the interaction of first nucleic acids with a second nucleic acids.

The term "biological data" as used herein refers to refers to functional annotations, or other annotations, name of a particular nucleic acid sequence, or other characteristic data of a nucleic acid.

The terms "associate", "link", "assign" as used herein all refer to a connection between data or physical objects.

The term "orthologs" as used herein denotes sequences, genes or molecules belonging to at least two species. In addition, these sequences, genes or molecules derive from a common ancestral sequence or from a common ancestral gene and have conserved the same function in each of the species.

The term "paralogs" as used herein refers to sequences, genes or molecules that derive from a duplication of a common ancestral sequence or of a common ancestral gene. In addition, these sequences, genes or molecules exhibit great sequence similarity and are present as at least two copies in the genome of a species.

The term "5' region of the microRNAs" as used herein refers to seven consecutive nucleotides starting at position 1 and ending at position 7 (positions included). At position 1, the term "5' terminal end of the microRNAs" is also used.

The term "3' region of the microRNAs" as used herein refers to the 10 to 18 consecutive nucleotides starting at position 8 up to the last nucleotide of the microRNA (positions included). Depending on the size of each microRNA, the last nucleotide may have the position from 17 to 25.

The terms "complementary" or "complement thereof" are used herein to refer to the sequences of a nucleic acid which are capable of forming Watson & Crick base pairing with another specified nucleic acid throughout the entirety of the complementary region. This term is applied to pairs of nucleic acid based solely upon their sequences and not any particular set of conditions under which the two polynucleotides would actually bind.

As used herein, the terms "complementary" or "complement" interchangeably refer to 100% antisense sequence identity.

The term "degree of complementarity" as used herein refers to the number or percentage of nucleotides that can pair between two nucleic acid sequence segments. Preferably, the pairings accepted are either of Watson-Crick type or of Wobble type (G-U pairings).

The term "similarity" as used herein refers to the degree of resemblance between two sequences.

The term "mismatches" as used herein defines positions along two aligned sequence segments that are different between these two segments.

The term "interaction" as used herein refers to any property or value that involves or corresponds to an exchange of energy between two molecules.

The term "correlation matrix" as used herein refers to an organized set of data that relates certain biological data to one or more nucleic acids. The term a "distance matrix" as used herein refers to an organized set of data that contains values of separation between pairs of nucleic acids. These structures may be any structure known to those skilled in the art, such as, but not limited to, a matrix.

The term "cluster" as used here refers to any set of nucleic acids that have been identified as having a sufficient proximity to be organized into a single group, family, or set. The nucleic acids of a cluster may designated as having common biological functions.

The term "3'UTR" as used herein denotes a noncoding region of the transcript of a messenger RNA. This region extends from a STOP codon to the end of a polyadenylation signal.

As used interchangeably herein, the terms "nucleic acid", "oligonucleotides", and "p olynucleotides" include RNA, DNA, or RNA/DNA hybrid sequences of more than one nucleotide in either single-stranded or double-stranded form. The term "nucleotide" as used herein as an adjective to describe molecules comprising RNA, DNA, or RNA/DNA hybrid sequences of any length. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar. However, the polynucleotides of the invention are preferably comprised of greater than 50% conventional deoxyribose nucleotides, and most preferably greater than 90% conventional deoxyribose nucleotides. The nucleic acids of the invention may be prepared by any known method, including synthetic, recombinant, ex vivo generation, or a combination thereof, as well as utilizing any purification methods known in the art.

The term "nucleic acid family" refers to a set of nucleic acids sharing common structural and functional features. For instance, tRNAs, rRNAs, snRNAs, snoRNAs, mRNAs and miRNAs represent different nucleic acid families.

The term "functional family" refers to a cluster of microRNAs that share a common functionality. This cluster may result at a branching node of a dendrogram at a specific depth, e.g., a depth of 3. This cluster may also result from a certain "functional similarity" issued from the "distance matrix," such as a given percentage.

The term "functional group" also refers to a cluster of microRNAs that share a common functionality. In some contexts, a "functional group" has less of a "functional similarity" than a "functional family". For instance, this cluster may result at a branching point at a larger depth than that of a "functional family", e.g., a depth of 4. This cluster may also result from a certain "functional similarity" issued from the "distance matrix," such as a given percentage.

The term "functional profile" refers to a set of functions or, in an equivalent manner, a set of biological phenomena.

General or current methods/protocols in molecular biology can be particularly found in the following references:
a) Sambrook and Russell, Molecular Cloning: A Laboratory Manual, 2001, Cold Spring Harbor Laboratory Press.
b) Bowtell and Sambrook, DNA Microarrays: A Molecular Cloning Manual, 2003, Cold Spring Harbor Laboratory Press.
c) Ausubel, et al., Current Protocols in Molecular Biology, 1987-2006, John Wiley Interscience.
d) Stirling and Bartlett, PCR Protocols, 2003, Humana Press.

BRIEF DESCRIPTION OF THE DRAWINGS

FIG. 7 is a table obtained illustrating for different microRNAs their potential target(s), the protein(s) produced, and the function(s) performed according to an embodiment of the present invention.

FIGS. 9A and 9B illustrate correlation matrices according to an embodiment of the present invention.

FIG. 12 is a table showing microRNAs identified as belonging to specific functional families in accordance with an embodiment of the present invention.

FIG. 13 is a table showing microRNAs identified as belonging to specific orphan functional families in accordance with an embodiment of the present invention.

FIG. 14 is a table showing functional families identified as belonging to specific functional groups in accordance with an embodiment of the present invention.

FIG. 15 is a table showing paralogous microRNAs identified as belonging to specific functional families in accordance with an embodiment of the present invention.

FIG. 16 is a table illustrating the fact that the method of the invention makes it possible to show that, for paralogous microRNA groups, the sequence differences can thus result in more or less substantial functional differences between each paralog of a group.

DETAILED DESCRIPTION

Figure 1:
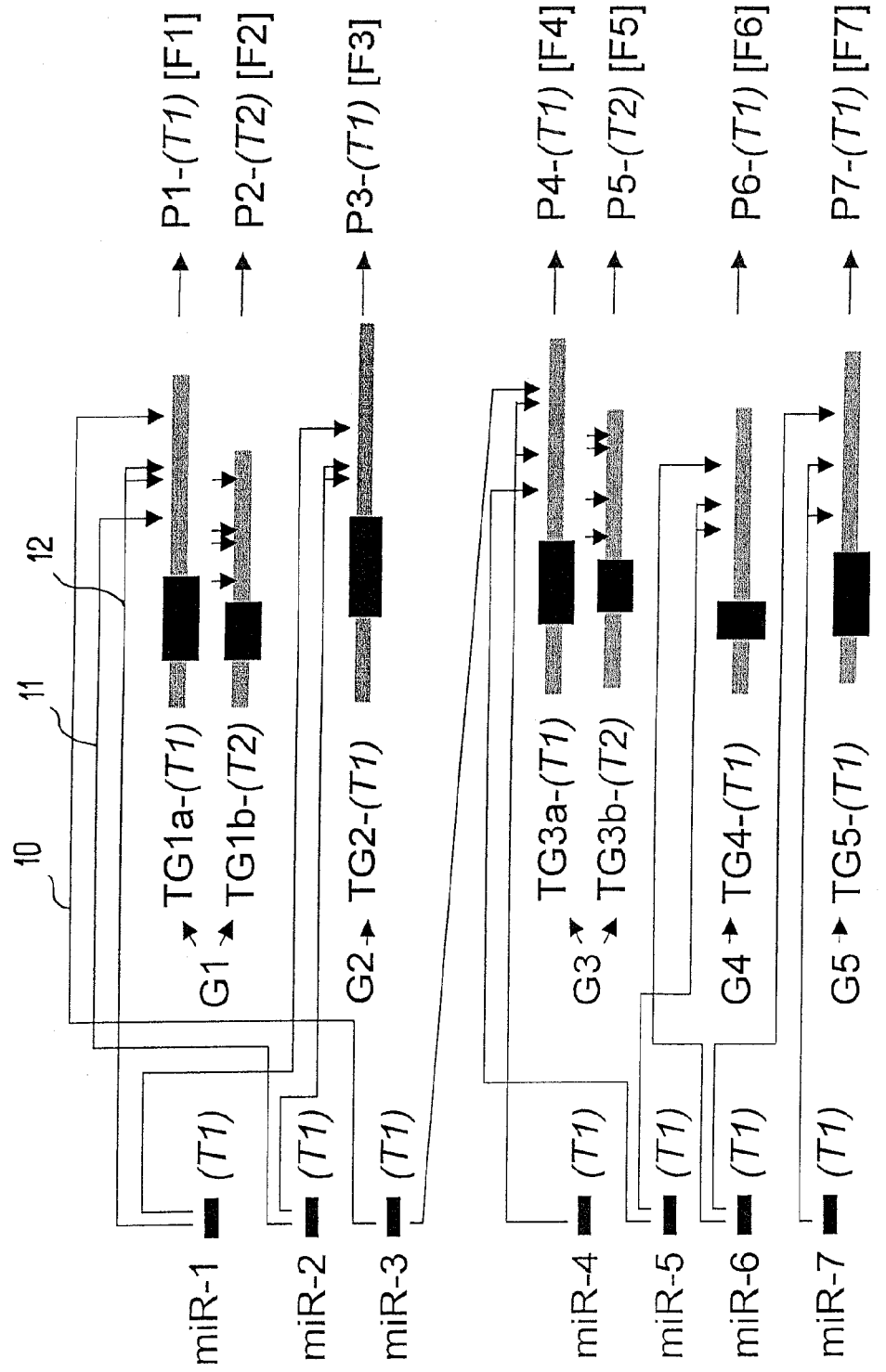
FIG. 1 illustrates schematically a principle according to which a microRNA interacts with one or more messenger RNAs so as to control a biological phenomenon by means of regulation of expression of a protein according to an embodiment of the present invention.

This invention provides methods, systems, and apparatus for identifying the biological functions of a set of nucleic acids (such as miRNA) and the mechanisms by which the biological functions are achieved, e.g., the true target sequences of the nucleic acids, based on biological data of their target nucleic acids. In one aspect, a networking mechanism (microRNA code) of the miRNA is identified to determine which miRNAs act in combination to cooperatively regulate a particular cellular/biological process. In one embodiment, a clustering based on the information belonging to the target (gene, transcript, protein) allows grouping together those miRNA acting together. For this particular group of miRNAs, those targets that are shared or that share a significant part of information are predicted as true targets, and others as off-targets.

The invention thus has many advantages described below in a non-limiting manner. The role of microRNAs in pathologies in which they are implicated may be understood and exploited not only for research and therapeutic purposes. These new key molecules of regulatory mechanisms that are directly involved in pathologies and new molecular markers associated with the development of numerous pathologies (for example: biological, diagnostic, prognostic markers) may be discovered. Also, newly developed drugs can target new molecules and/or their targets for the prevention of cure of patholgies.

New classes of tools may be designed and produced. Synthetic microRNAs that must target a set of chosen genes may be designed by virtue of the knowledge of the microRNA code. More generally, new biological experiments may be constructed from such knowledge of the microRNA code. Embodiments give the opportunity to act on this biological process by inducing an over/down expression of several miRNAs. Embodiments may also allow driving the differentiation process from stem cells to differentiated cells.

I. Introduction

MicroRNAs (miRNAs) constitute a large family of very small molecules. In humans, their number is currently estimated as more than 1000 and their size is typically between 17 and 25 nucleotides. MicroRNAs can be produced from endogenous genes which are transcribed in the form of long primary precursors, called pri-microRNAs (or pri miRNAs). Each pri-microRNA is cleaved by a nuclease, the Drosha nuclease, for example, to give a second precursor approximately 70 nucleotides long, called pre-microRNA (or pre-miRNA).

The pre-microRNA is exported to the cytoplasm of at least one cell, where a nuclease, for example, the Dicer nuclease, allows the microRNA to be produced. The majority of microRNAs are subjected to two types of regulations: firstly, a temporal regulation and, secondly, a spatial regulation. The temporal regulation depends on cell, tissue and organism growth, differentiation and development steps. The spatial regulation reflects, for its part, the fact that microRNAs are specifically expressed in a genus, a tissue type or a cell type (Reinhart, 2000).

A characteristic of microRNAs is their antisense capacity, i.e. their capacity to exert one or more specific biological phenomena by virtue of more or less extended base pairings with predetermined regions of respective target molecules. These target molecules and these regions constitute what is commonly referred to as target messenger RNAs (mRNAs) and target recognition sequences (TRSs), respectively. More specifically, the abovementioned pairings typically occur in 3'UTR regions of the target messenger RNAs. Depending, in particular, on the exact location and the type of complementarity (complete or partial), microRNAs will lead to either a repression of the translation of the mRNAs, or a destruction of the latter. Thus, microRNAs can control the expression of proteins produced from messenger RNAs (mRNAs).

As a result, miRNA have the ability to determine how, when and where genes are expressed and also the ability to coordinate the interactions between these genes. Even more generally, microRNAs orchestrate numerous aspects of cell and organism development and function, and play key roles in the regulation of fundamental cell mechanisms (Brennecke et al., 2005; Chen et al., 2004; Esau et al., 2004; Yekta S. et al., 2004).

By way of illustration, numerous experiments in animals have demonstrated the involvement of microRNAs in event cascades resulting in cell and tissue differentiation. In addition, it has been demonstrated that microRNAs regulate various metabolic pathways and physiological processes such as cell proliferation and apoptosis (Houbaviy et al., 2003, He L. et al., 2004; Kasashima K et al., 2004; Xu P. et al., 2004; Bartel, 2004). Moreover, it is increasingly recognized that microRNAs have a direct role in the development of pathologies, in particular cancers.

For example, in lung adenocarcinoma, a reduction in the expression of the let-7 microRNA is associated with a significant shortening of post-operative survival, whereas overexpression of the same microRNA in a lung adenocarcinoma cell line inhibits growth of the cancer cells in vitro (Takamizawa J. et al., 2004). Similarly, two microRNAs [miR-143 and miR-145) show a substantial reduction in accumulation at certain stages of colorectal cancers (Michael et al., 2003). Another example concerns deletions and a decrease in expression of the miR-15 and miR-16 microRNAs that occur in the majority of leukemias of the B cell chronic lymphocytic leukemia type (approximately 68%) (Calin et al., 2002; Calin et al., 2004). Also, an overabundance of microRNAs of the mir-17-92 family in human lymphomas and the development of cancer in mice in the event of overexpression of these microRNAs have been discovered (He L. et al., 2005).

Additionally, microRNAs may be involved in neurological and neurodegenerative diseases (Dostie et al., 2003). Yet other examples illustrate the importance of microRNAs in organisms. In particular, a link has been established between microRNAs and c-Myc, a proto-oncogene which encodes a transcription factor and regulates cell proliferation, growth and apoptosis (O'Donnell et al., 2005).

As indicated above, microRNAs are also involved in metabolic diseases. MicroRNAs specific for the pancreas can regulate insulin secretion. For example, miR-375 is a regulator of insulin secretion and could constitute a novel pharmaceutical target for the treatment of diabetes (Poy et al., 2004).

To control a biological phenomenon, such as those mentioned above, one may consider that microRNAs can act as a network (in combination) and cooperatively. Thus, according to such a hypothesis, a set of various microRNAs that cooperate with one another as a network to control one or more phenomena could be defined. Such a set could be designated by a microRNA code name.

For example, experimental results have shown that the tissue specificity of gene expression can correspond to the expression of a specific set of microRNAs for each tissue [Hobert O, 2004; Doench et al., 2004), which would confirm the existence of a microRNA code. In particular, experimental results have shown that a mammalian gene can be regulated in a coordinated manner by several specific co-expressed microRNAs (Sempere et al., 2004).

An important step today is therefore that of confirming the existence of microRNA codes and of identifying the biological phenomena that specific microRNA codes control. In animals in general and humans in particular, it is not known, except for a few rare exceptions, how to associate one biological phenomenon or another with a single microRNA or, a fortiori, with a set of microRNAs.

One of the reasons lies in the few structural constraints that are exerted on the microRNA-mRNA duplexes, which are commonly referred to with a target recognition sequence (TRS) that interacts with the microRNA. For example, in animals, unlike plants, these duplexes contain numerous mismatches, internal loops, and Wobble-type pairing (G:U). In addition, the number of consecutive pairings is very short (typically between 8 and 10 nucleotides located at the 5' end of the microRNA (Lai et al., 2002).

Identification of the targets, i.e. of the messenger RNAs, of the microRNAs by means of a simple molecular biology approach is therefore extremely difficult, or even impossible at this time. In an attempt to address such a problem, bioinformatic tools known, for example, under the following names: "Pictar" (Krek et al., 2005); "DIANA-microT" (Kiriakidou et al., 2004); "TargetScan" (Lewis et al., 2003); "MiRanda" (Enright et al., 2003), have been developed. These tools create binary relationships between microRNAs and their respective potential target recognition sequence(s). In other words, they associate an appropriate potential target recognition sequence list with each microRNA taken individually and, in the end, provide a gross list of these associations.

Although they have been useful in many ways, the existing tools have drawbacks. For each microRNA, they result in a number of potential target recognition sequences that is much too great, which limits the exploitation of the results. Specifically, it is difficult to differentiate, in these large lists, the real biological targets from the background noise.

Moreover, there is a great disparity in results between these tools for the same microRNA. For example, for the miR-15 microRNA, the "Pictar" tool provides a list of 746 possible targets, whereas, in "miRBase", "TargetScan" and "MiRanda", the list goes to 3918, 596 and 3456 potential target recognition sequences, respectively. For the miR-19 microRNA, the number of potential target recognition sequences provided is, respectively, 677, 5528, 527 and 1453.

Another drawback of these tools is that they are based on approaches that have not been the subject of a biological or functional validation. Moreover, although they make it possible to obtain lists of potential target recognition sequences, these tools do not make it further possible to decipher microRNA codes.

II. microRNA Code

Referring now to FIG. 1, one manner in which a microRNA is capable of exercising a function (controlling a biological phenomenon) in an organism has been illustrated schematically by way of a reminder. In this figure, a gene, noted G1, provides two transcripts TG1a and TG1b, which are messenger RNAs. As also illustrated, each of them is specific for a respective tissue T1 and T2 and each produce a respective protein P1 and P2 that have one or more functions.

In this example, the protein P1 exercises a function F1 and the protein P2 exercises a function F2. Given that a microRNA can interact only with a messenger RNA that is coexpressed in the same tissue, a microRNA such as miR-1 in the tissue T1 can interact only with the TG1a messenger RNA, and not the TG1b messenger RNA. It will also be noted that this microRNA can interact with other messenger RNAs.

For example, within tissue T1, mir-1 interacts with a TG2 messenger RNA, which is capable of producing a protein P3 having a function F3. Thus, as illustrated, the miR-1 microRNA is involved in the production of the proteins P1, P2 and P3. Consequently, miR-1 is involved in the exercising of several functions F1, F2 and F3. Such a piece of information can be advantageously used to decipher a microRNA code.

In addition, embodiments of the invention are capable of determining which set of microRNAs are involved in which functions. For example, in the case illustrated in FIG. 1, graphic links 10, 11 and 12, show that the function F1 is regulated by the set of microRNAs miR-1, miR-2 and miR-3. Thus, these three microRNAs constitute a microRNA code for this function F1.

It will be noted here that the method of the invention is typically integrated into a computer program that is run on a processing system. This program is recorded on a recording medium such as, for example, a disk, a hard drive, a flash drive, or other suitable medium now known or discovered in the future.

III. Identifying microRNA Codes and their Biological Function

Accordingly, embodiments of the present invention provide information to identify microRNA codes and their biological function. Such information may include which microRNA are involved in the production, regulation, or expression of which proteins, genes, transcripts, or other nucleic acids and/or functions associated with such nucleic acid families.

Figure 2:
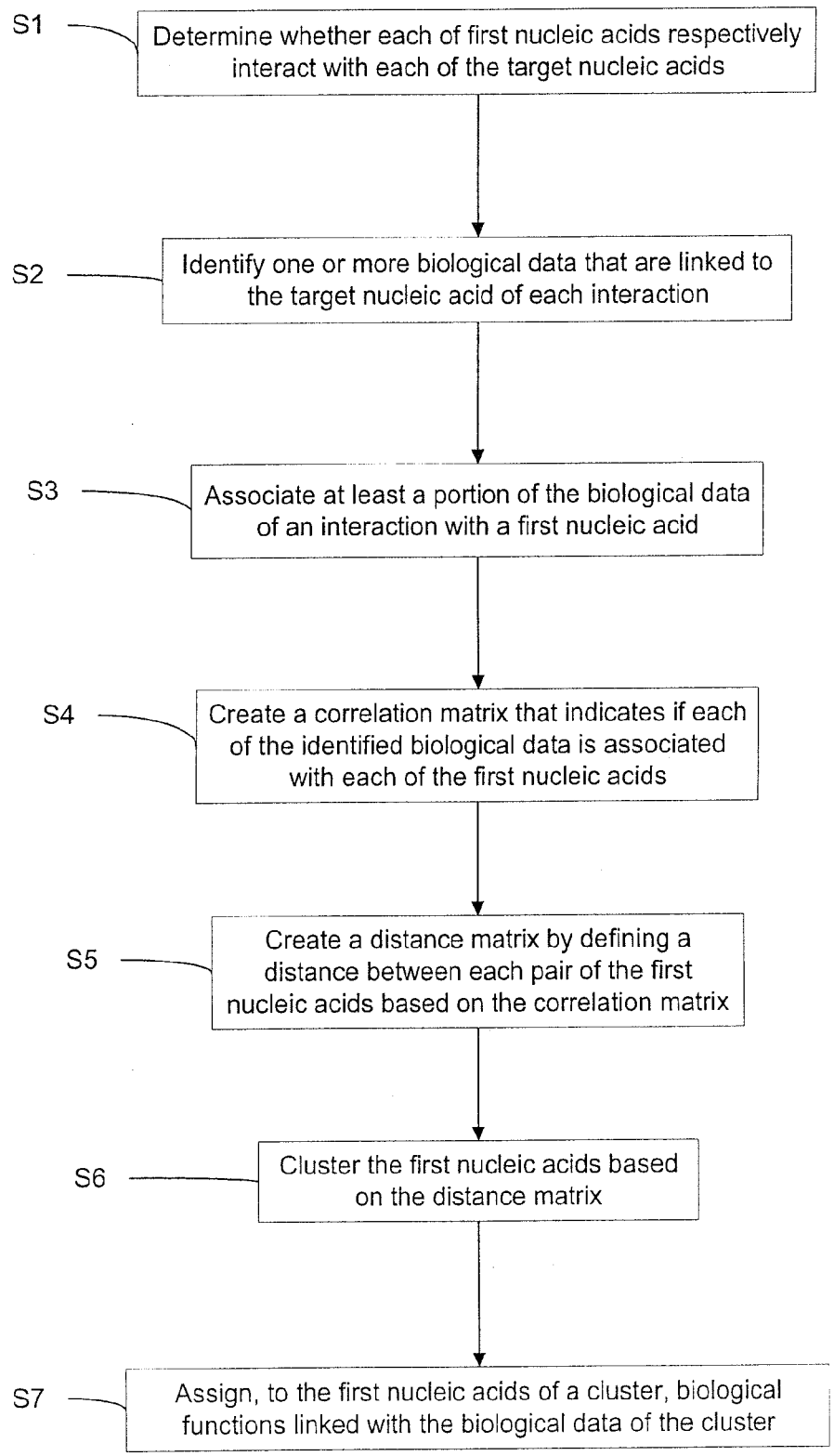
FIG. 2 illustrates a method of identifying microRNA codes and associated biological functions according to an embodiment of the present invention.

FIG. 2 illustrates a method 200 of identifying microRNA codes, which may be defined as a cluster or part of a cluster, and associated biological functions according to an embodiment of the present invention. In one aspect, the method can analyze a set of first nucleic acids that can interact with at least one target portion of respective target nucleic acids to identify at least one cluster of the first nucleic acids that potentially cooperate with one another so as to affect one or more biological functions.

In step S1, for each of the first nucleic acids, it is determined whether that first nucleic acid respectively interacts with each of the target nucleic acids. In one aspect, the first nucleic acids and the target nucleic acids are from different nucleic acid families. In one embodiment, the interactions involve complementarity; however, the interactions may be of any type. In step S2, for each interaction, one or more biological data that are linked to the target nucleic acid of that interaction are identified. The biological data may simply be a name of the mRNA or the TSR of the mRNA, an associated gene, functional annotations associated with the target or other biological data as explained herein.

In step S3, for each of the first nucleic acids, at least a portion of the biological data linked to the target nucleic acids with which that first nucleic acid interacts is associated with that first nucleic acid. In one aspect, only biological data that is significant to a particular nucleic acid is associated with that nucleic acid. In step S4, a correlation matrix that indicates whether each of the identified biological data is associated with each of the first nucleic acids is created.

In step S5, a distance matrix by defining a distance between each pair of the first nucleic acids based on the correlation matrix is created. In step S6, the first nucleic acids are clustered based on the distance matrix. In step S7, a portion of a set of biological functions linked with the biological data associated with the first nucleic acids of the cluster are assigned to the first nucleic acids of a cluster. In one embodiment, where the biological data includes functional annotations, the biological functions may correspond to the functional annotation data. In another embodiment, the assigned biological functions may correspond to the true interactions between a microRNA and select target nucleic acids.

Embodiments of the present invention may be applied to all known miRNA or to any subset of miRNA chosen on the basis of any criteria. For example, a set of miRNA over-expressed (or down-regulated) in a specific physiological condition, or in one tissue as compared with another may be chosen. This method is also applicable to other families of nucleic acids, particularly non-coding RNAs that might be: relatively abundant, interact (e.g., through complementarity) with another family of nucleic acids, have a networking mode of function, have a weak interaction (many off-targets), and the targeted nucleic acids are described by a rich set of information. Thus there may be many regulatory RNA (some which have not yet been discovered), the analysis of which may benefit from methods of this invention.

A. Determining Interactions Between Different Families of Nucleic Acids

Figure 3:
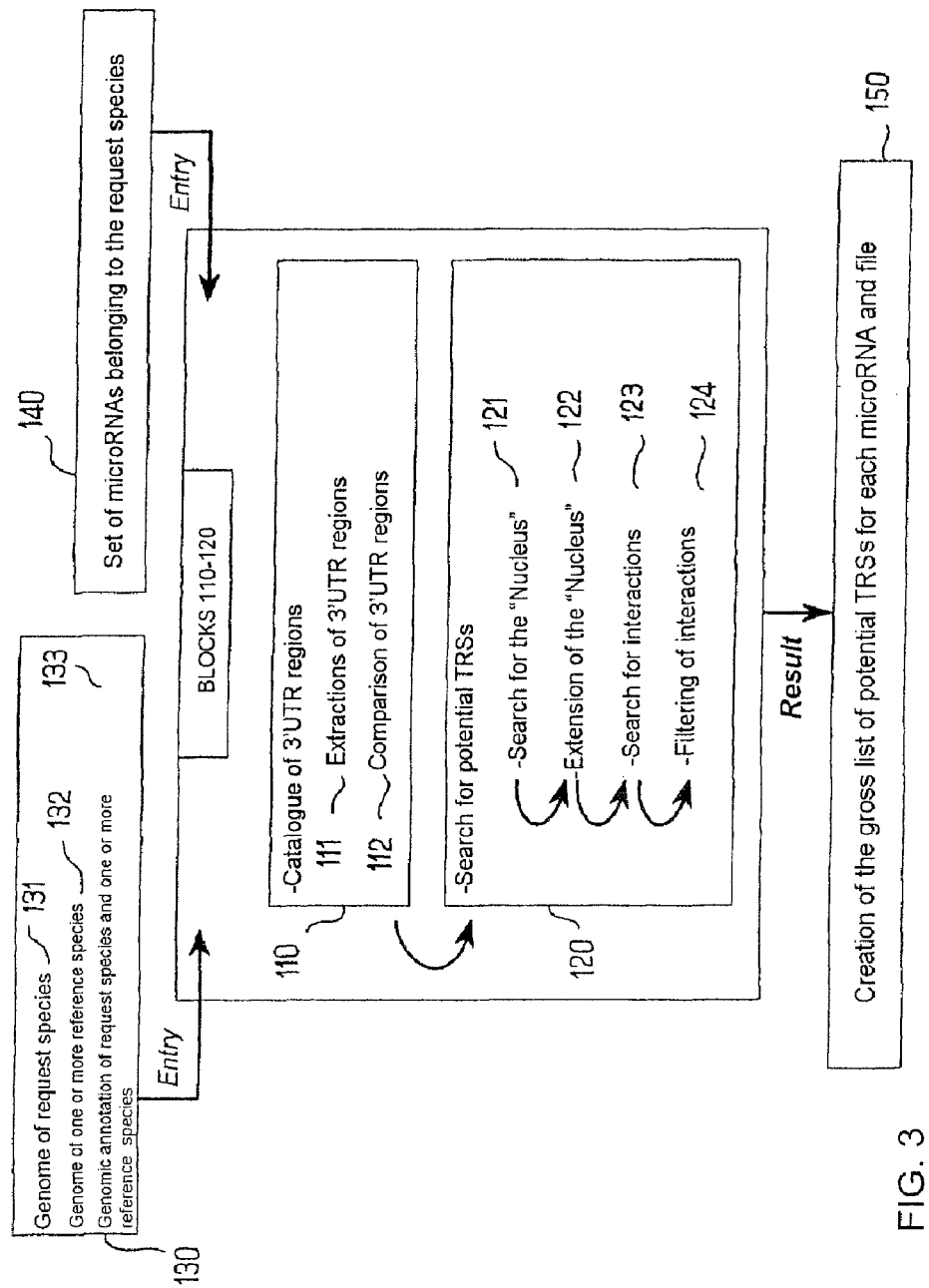
FIG. 3 illustrates a method of determining interactions between first nucleic acids and the target nucleic acids according to an embodiment of the present invention.

FIG. 3 illustrates a method of determining interactions between first nucleic acids and the target nucleic acids according to an embodiment of the present invention. In this example, microRNAs are the first nucleic acids and messenger RNAs are the target nucleic acids, with target recognition sequences (TRSs) corresponding to target portions of the messenger RNAs. In aspect, a gross list of potential target recognition sequences (TRSs) is produced. As illustrated in FIG. 3, embodiments comprise various blocks of steps.

1. Catalog Target Portions (Block 110)

In a block 110, a phylogenetic approach is used, in particular, to identify the sequences located in the 3'UTR regions of messenger RNAs (for example, orthologous RNAs) that are conserved between a request species (i.e. the species to be analysed) and one or more reference species. By way of example, the request species may be man (Homo sapiens) and a reference species that of mouse (Mus musculus). In one embodiment, a degree of similarity greater than or equal to 80% is used in the phylogenetic approach.

Block 110 can produce a catalogue of the sequences located in the 3'UTR regions of the request species corresponding to the similarity conditions defined above. In one embodiment, block 110 breaks down into two steps. In step 111, the sequences corresponding to the 3'UTR regions of the request species and of the one or more reference species are extracted from the sequence of the corresponding genome, using genomic annotations provided by an appropriate database.

In FIG. 3, the database is represented in a block 130. This block 130 includes searching databases so as to provide the necessary information to block 110. In one embodiment, block 130 includes searching in databases relating to the request species 131, relating to the one or more reference species 132, and relating to the genomic annotations 133 of at least all the species involved. In an embodiment, the database commonly called "Ensembl" (Hubbard et al., 2005) is used. The 3'UTR sequences are stored in a file that forms a database and is called, for example, the "3'UTR database".

In step 112, the 3'UTR sequences recorded in the "3'UTR database" are compared between the request species and the one or more reference species, for each group of orthologous 3'UTR sequences. The 3'UTR sequences of the request species exhibiting a certain degree of similarity, e.g., greater than or equal to 80%, with the one or more reference species are stored in a second file that forms a database. This second file is, for example, called "conserved 3'UTR database". As illustrated in FIG. 3, a block 120 can follow block 110.

2. Search for Potential TRSs (Block 120)

An aim of the second block 120 is to search for possible pairings between microRNAs and the 3'UTR sequences recorded in the abovementioned second file (conserved 3'UTR database). In one aspect, block 120 produces a gross list of the potential target recognition sequences (TRSS) for each microRNA of the request species analyzed. In one embodiment, block 120 breaks down into four steps.

In step 121, a search determines sequences in the "conserved 3'UTR database," that are strictly complementary to a region of a microRNA containing the nucleotides from position 2 to position 7 (inclusive). Herein, the positions of the miRNA start from "1" at the 5' terminal region and end at the 3' terminal region. The data related to a specified set of microRNAs belonging to the request species are provided by a block 140, where the specified set may be all known miRNA are a subset satisfying a certain criteria.

In a first substep of step 121 (not represented), the reverse-complement of said sequence containing the nucleotides of positions 2 to 7 inclusive is generated for the microRNA in question. In a second substep of step 121 (not represented), the sequences containing the reverse-complement are compared to each of the sequences recorded in the "conserved 3'UTR database" file. In one embodiment, the sequences that correspond to the following two criteria are stored: (1) all the positions of the two sequences compared must be paired, and (2) only pairings of Watson-Crick type (AU, AT, GC) and pairings of Wobble type (GU) are accepted. Other criteria within the scope of those skilled in the art may be used.

Figure 4:
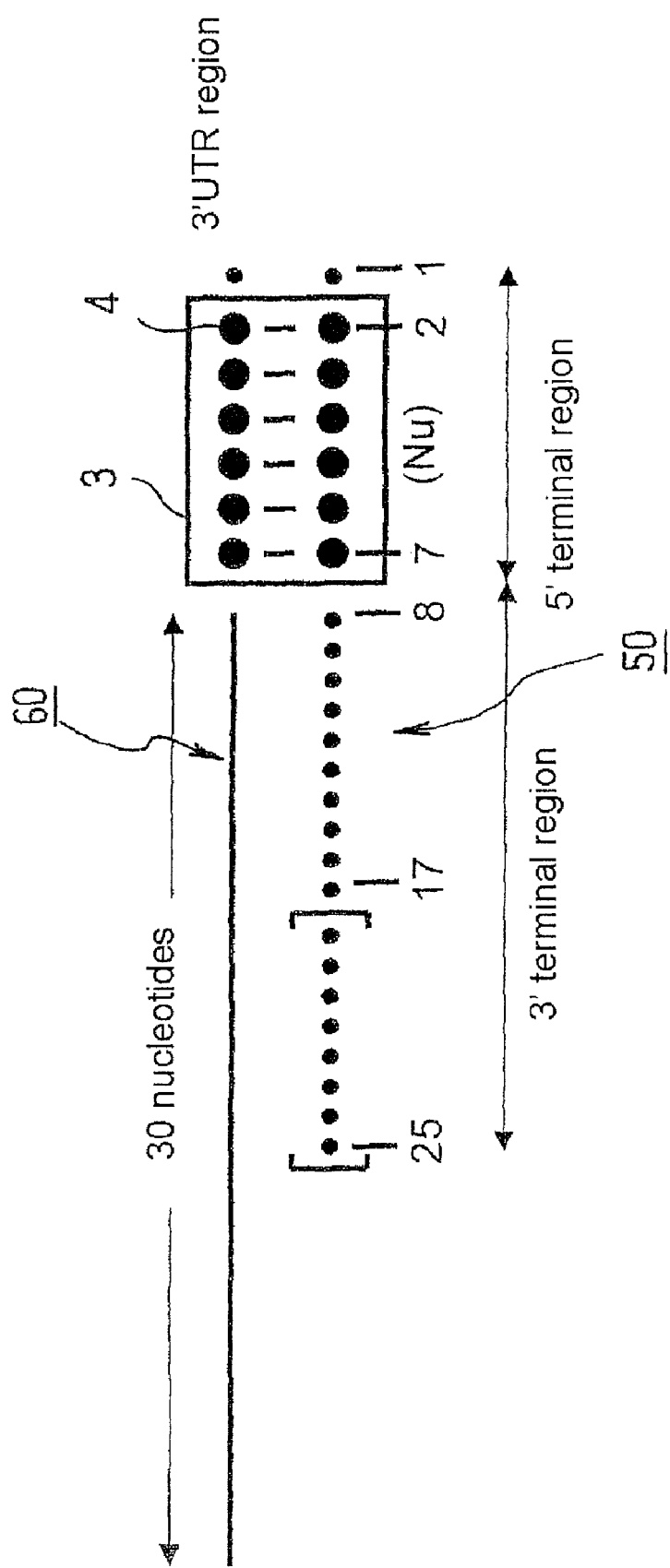
FIG. 4 illustrates schematically the interaction between a microRNA and a messenger RNA at two regions called "5' terminal region" and "3' terminal region" according to an embodiment of the present invention.

FIG. 4 illustrates schematically the interaction between a microRNA and a messenger RNA at two regions called "5' terminal region" and "3' terminal region" according to an embodiment of the present invention. A first zone of complementarity on the 3'UTR will, in the subsequent text, be referred to as the nucleus (Nu) 3. A microRNA 50 having interactions with a messenger RNA 60 can in particular be seen. In one aspect, this interaction takes place at the nucleus (Nu) 3 corresponding to the 5' terminal region of the microRNA 50. Nucleus 3 is typically 6 nucleotides long in size. One of the nucleotides is denoted by the reference 4 in FIG. 4. In one embodiment, the nucleus includes positions 2 to 7 on the microRNA 50, and positions N to N-6 on the messenger RNA 60 in its 3'UTR region. The positions N to N-6 may occur at any point in the 3'UTR region are only labeled here for convenience and clarity.

Figure 5:
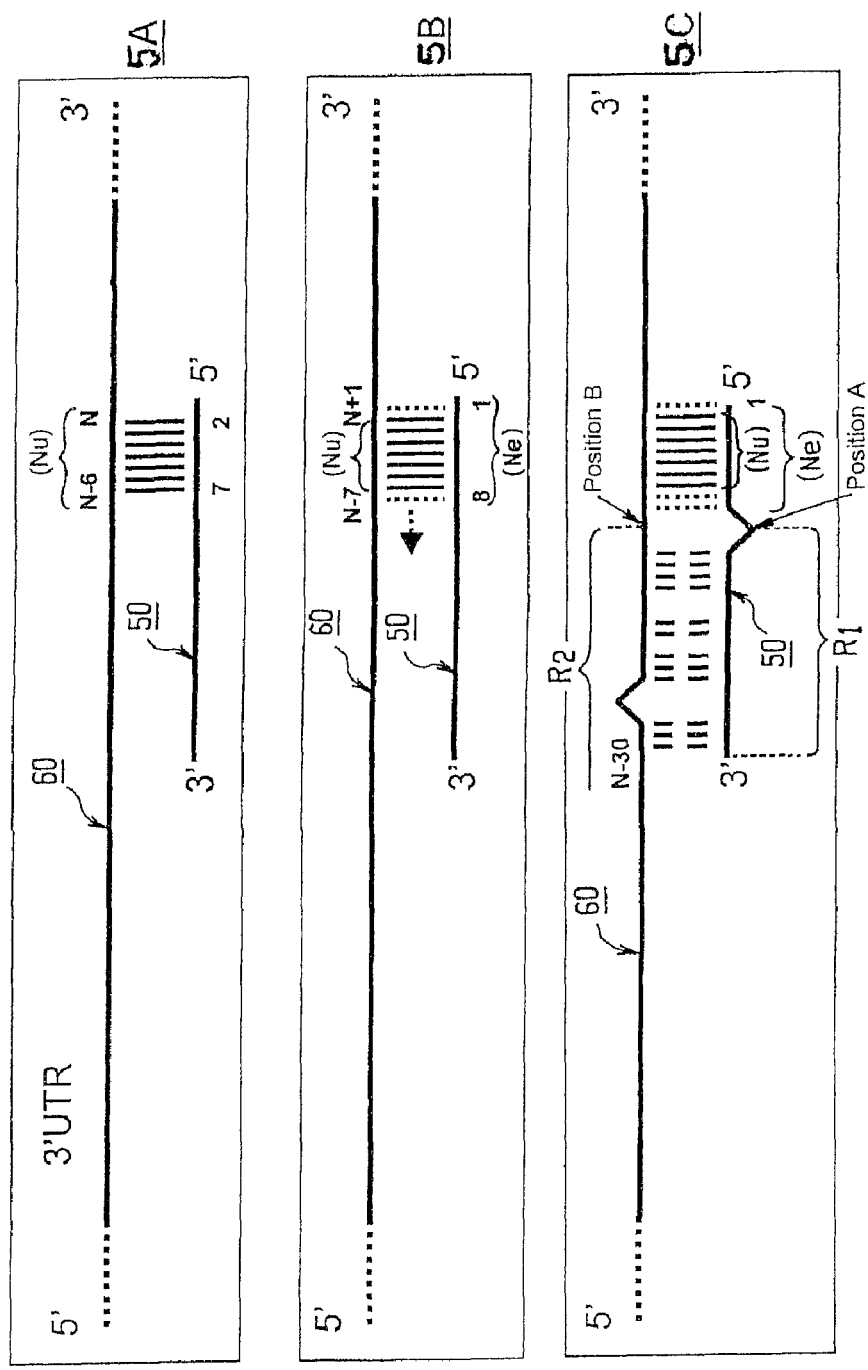
FIGS. 5A-5C illustrate, respectively, steps for searching for a nucleus and an extended nucleus according to an embodiment of the present invention.

FIGS. 5A-5C illustrate, respectively, steps for searching for a nucleus and an extended nucleus according to an embodiment of the present invention. Once the nucleus of the microRNA has been identified as illustrated in FIG. 5A, it is determined, in a second step 122, whether this nucleus can be spatially extended. To determine the extended nucleus, possible new consecutive pairings on either side of the nucleus (Nu) are sought (see, in particular, FIGS. 5B and 5C). In one embodiment, a new pairing occurs if it meets a predetermined criterion. The criterion may be the following: (1) only Watson-Crick pairings AU, AT and GC and Wobble pairings (GU) are valid, and (2) the extended nucleus (Ne) contains only consecutive pairings.

In a first substep (not represented) of step 122, the pair of nucleotides at position 1 of the microRNA 50 and at position N+1 of the 3'UTR sequence 60 is analyzed. If the complementarity is verified, the position N+1 is part of the extended nucleus (Ne). Also, the pair at position 8 of the microRNA 50 and at position N-7 of the 3'UTR sequence 60 is then analyzed. If the complementarity is verified, the position N-7 is also part of the extended nucleus (Ne).

The following pair of nucleotides, i.e. at position 9 of the microRNA 50 and at position "nucleus-8" (N-8) of the 3'UTR sequence 60, are also analyzed, and so on until the abovementioned pairing conditions are no longer observed. The first zone of complementarity between the microRNA 50 and the 3'UTR target recognition sequence 60 therefore corresponds to the extended nucleus (Ne) thus identified. In this first zone, the degree of interaction (complementarity) between the microRNA 50 and the messenger RNA 60 is at a maximum. In one embodiment, in this first zone, no break in pairing (interaction) between nucleotides of the messenger RNA and of the microRNA is permitted.

In step 123 (see FIG. 4C), a second zone is identified, in which one or more breaks in pairing (interaction) between nucleotides of the messenger RNA and of the microRNA are permitted. To this effect, a set of nucleotides that are partially complementary between the region R1 on the microRNA and the region R2 the 3'UTR sequence 60. Region R1 extends from the position "extended nucleus +1" (position A) up to the 3' end. Region 2 extends from the position "extended nucleus −1" (position B), over a length of up to 30 nucleotides towards the 5' end, is identified on the 3'UTR sequence 60. In one embodiment, in this step 123, non-consecutive pairings of Watson-Crick (AU, AT/AU, GC) and Wobble (GU) type only are accepted.

In step 124, a free energy of pairing between the microRNA 50 and the 3'UTR sequence 60 is determined. The pairing may be done using both the first and second zones. In one embodiment, these two zones are selected as a potential target recognition sequence (TRS) for the microRNA in question if the free energy of pairing, between this microRNA and the 3'UTR sequence 60, is less than or equal to a predetermined threshold value, such as −16.4 kcal/mol.

All the steps of the block 120 that have just been described can be repeated: (1) for all the nuclei (Nu) identified for this microRNA on a single sequence contained in the "conserved 3'UTR database" file, (2) for all the other sequences of the "conserved 3'UTR database" file, and (3) for each microRNA. The set of potential target recognition sequences (TRSs) thus identified constitute a gross list 150 which can be stored in a file called "gross list".

Each possible interaction can be stored as a "microRNA-possibleTRS" associated datum. In the remainder of the text, reference will be made, for this associated type of data, to a "microRNA-possibleTRSs" pair. If several target recognition sequences are identified for the microRNA, the file contains as many associated data for this microRNA as there are possible sequences found. Thus, this gross list contains datum for the possible TRSs that may truly interact with each corresponding miRNA. According to the invention, the gross list 150 provided by the block 120 is then processed in a block 200 that is in large part illustrated in FIG. 6.

B. Identifying Biological Data Linked to Target Nucleic Acids (Block 210)

In one aspect, the gross list is augmented with biological data. For each interaction pair (e.g., microRNA-possibleTRS), certain biological data that is linked to the possible TRS is identified. This biological data can be of many different types, including the mRNA for each possible TRS, functional annotation data linked to the mRNA, as well as pathway annotations or other annotations. Thus, instead of one character (the name of the gene), multiple characteristics (e.g., 18) that describe a gene may be used. This identification of biological data is denoted by step 210 of FIG. 6, which illustrates schematically the functional clustering of nucleic acids according to an embodiment of the present invention.

In one embodiment, data relating to the proteins produced by the transcript(s) targeted by the microRNA in question are identified for each "microRNA-possibleTRSs" pair of the gross list. Data of the "microRNA-possibleTRSs-protein" type are thus obtained. Data relating to the function(s) (F) linked to each of the proteins that were associated with the microRNA in question may also be identified with these "microRNA-possibleTRSs-protein" data.

In this text, reference will also be made to the expression "functional annotation" to denote the data relating to a function (F). The functional annotations can be extracted from a universally recognized standard vocabulary such as, for example, that of the database: "Gene Ontology" (GO) (Ashburner et al., 2000). The search of this database is illustrated in block 160 in FIG. 6. Of course, any other file or database containing functional annotations of genes or of their products could be used.

In one aspect of the present invention, an enhanced gross list of data of the "microRNA-possibleTRSs-protein-GO_functional_annotations" type is then obtained. This enhanced gross list is recorded in a file which contains as much data of this type as there are potential target recognition sequences (TRSs) present in said list.

FIG. 7 is a table obtained illustrating for different microRNAs their potential target(s), the protein(s) produced, and the function(s) performed according to an embodiment of the present invention. The table in this figure shows in particular the set of relationships from the microRNA to the function. It is, for example, seen that mir-1 interacts with TRS1, TRS2, TRS6; TRS1, TRS2, TRS6 produce, respectively, the proteins Prot A, Prot B, Prot D; Prot A exercises the functions A, B, C; Prot B exercises the functions A, C, D, etc.

In one embodiment, the protein is used as information for identifying the function(s) (F) exercised, but the datum relating to this protein may not be associated with the microRNA. In other words, the enhanced gross list can also be established with associated data of the "microRNA-possibleTRSs-GO_functional_annotations" type. In all cases, this list makes it possible to enrich the knowledge regarding the microRNAs. In fact, by virtue of the method, an enhanced gross list is provided which directly links a microRNA to a function (F) on which it is capable of acting.

According to a preferred embodiment of the invention, the enhanced gross list is analyzed taking into account the abovementioned functions (F) so as to deduce a piece of biological information on a microRNA code, i.e. a set, or subset, of microRNAs that appear in said list and cooperate preferentially with one another so as to exercise one or more specific functions. As mentioned above, such an analysis is also referred to, in this text, as "deciphering a microRNA code". In order to achieve this aim, the abovementioned block 200 preferably comprises three sub-blocks of steps referenced by the numbers 220, 230 and 240 in FIG. 5.

C. Associating Biological Data with Nucleic Acids (Block 220)

In one embodiment, all of the identified biological data for each microRNA-possibleTRSs is associated with the specific microRNA. In other embodiments, only data of a certain type such as only the functional data or the name of the mRNA (or the corresponding gene) is associated with the microRNA. In yet other embodiment, only significant biological data is ultimately associated with a microRNA. Thus, only a portion of the identified biological data is associated with the microRNA.

Figure 8B:
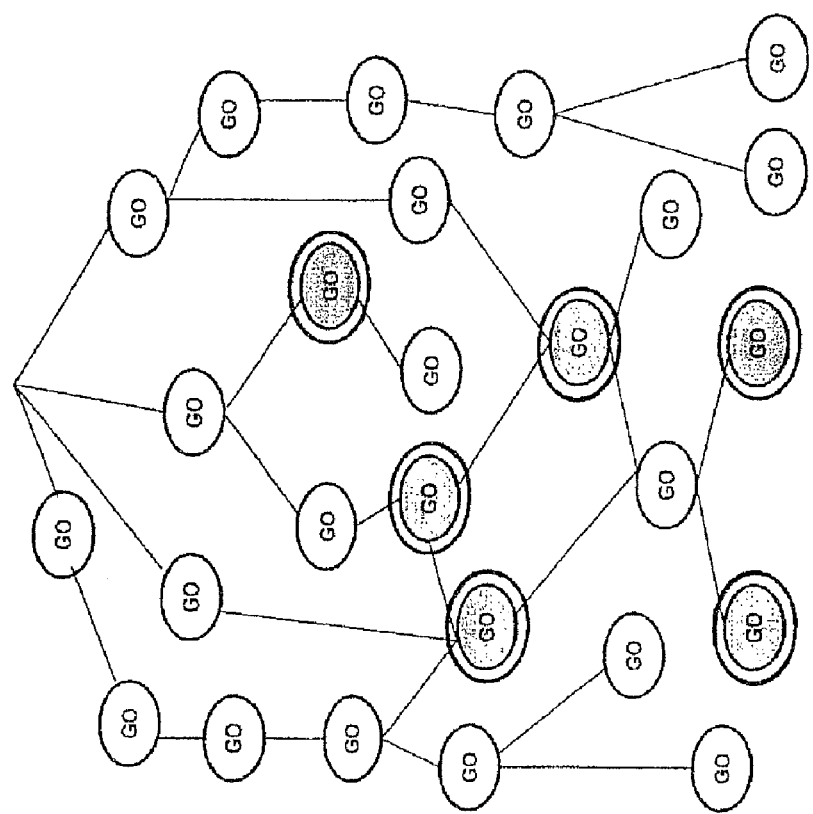
FIGS. 8A and 8B show relational trees of GO terms according to an embodiment of the present invention.
Figure 8A:
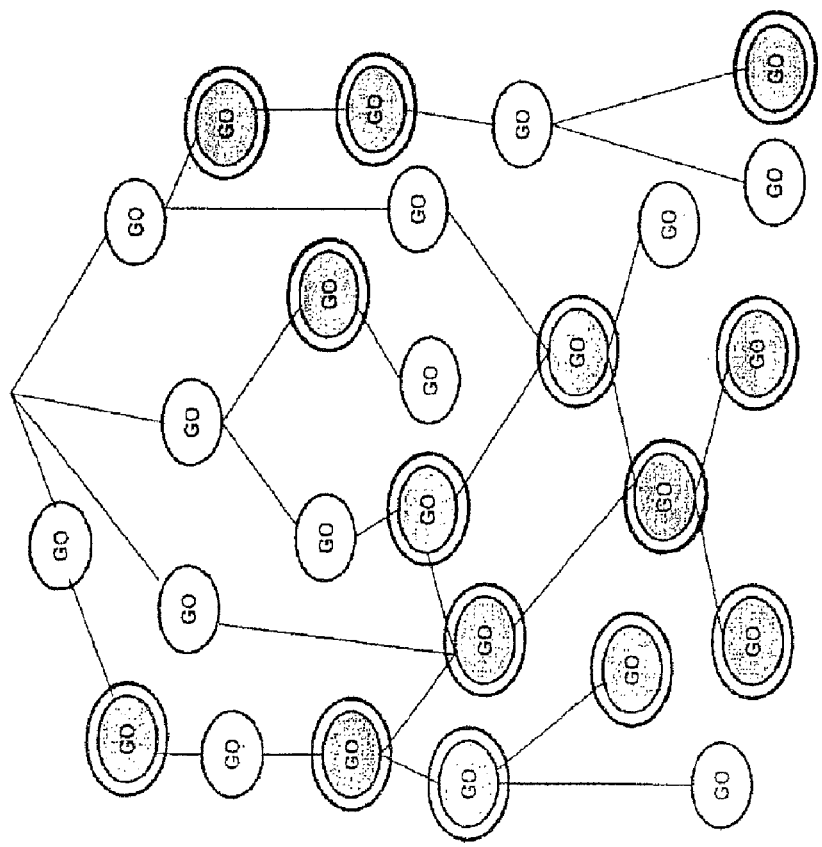

To the end of identifying significant biological data, the biological data is compared. FIGS. 8A and 8B show relational trees of GO terms according to an embodiment of the present invention. In a first step 221 of the subblock 220, all the functions or, by equivalence, all the GO terms, present in the enhanced gross list of the "microRNA-possible-TRSs-GO_functional_annotations" data are positioned on a tree as described by a consortium which ensures maintenance thereof and development thereof (Ashburner et al., 2000). Applied to the invention, this tree will be called "GO-microRNA-complete tree" (FIG. 8A).

The Gene Ontology database provides a controlled and standard vocabulary for detailing the function of genes in the following three domains: "cellular component"; "molecular function"; "biological process". Thus, each protein is characterized by a set of terms belonging to these three categories. In a GO tree, the GO terms of each of the three categories are associated with one another via lineage/ancestry linkages (in the form of an acyclic tree) allowing navigation between parent nodes, child nodes and the functional annotations associated with each node. On the GO-microRNA-complete tree in FIG. 8A, the GO nodes surrounded twice correspond to the GO terms that are observed for all miRNA-target associations. GO terms that are circled only once are all other GO terms which are stored in the Gene Ontology database, as only a subset of this complete list are observed.

In a second step 222 of the subblock 220, the functions, or GO terms, associated with each microRNA taken individually in the list of "microRNA-possible-TRSs-GO_functional_annotations" data are positioned on the "GO original complete" tree. As many trees of this type as there are microRNAs in said file are therefore generated. These trees, an illustration of which is given in FIG. 8B, are here referred to as "GO-microRNA-unique tree".

In a third step 223, the "GO-microRNA-unique" tree of each microRNA is compared with the "GO-microRNA-complete" tree so as to carry out a filtering of the significant GO terms. To this effect, it is possible to use a statistical method based on a hypergeometric law to calculate the significance of the GO terms present in each "microRNA-possibleTRSs-GO_functional_annotations" datum. Other statistical methods may be used as our well known to those skilled in the art.

In one embodiment, a statistical variable known as the p-value is calculated. In addition, the GO terms for which the value of the p-value variable is less than or equal to 0.05 are preferably considered to be significant. Only the significant GO terms may be kept in the remainder of the method. To this effect, a list of the significant GO terms associated with each microRNA is created. This list is stored in a file and comprises data of the "microRNA-possibleTRSs-GO_functional_annotations-significant" type.

D. Creating a Correlation Matrix with Associated Biological Data (Block 230)

The significant biological data along with its linkage to the TSRs and the corresponding miRNA may be used to create a correlation matrix to enable a functional classification of the microRNAs. To facilitate a comparison of the miRNA, the correlation matrix indicates whether each of the identified biological data is associated with each of the first nucleic acids. In this manner, miRNA with similar functionality based on the biological data may be identified. Thus, a microRNA code may be deciphered.

FIGS. 9A and 9B illustrate correlation matrices according to an embodiment of the present invention. In FIG. 9A, the matrix 900 has rows 910 that correspond to a set of miRNA. For ease of presentation, only three are shown. Columns 920 correspond to the identified biological data, and in this embodiment the biological data is the corresponding gene for the mRNAs in the gross list. The biological data could also simply be the name of the mRNA themselves. Matrix elements 930 contain an indication of whether a miRNA is associated with one of the genes 930, and thus whether a specific miRNA targets a particular gene or mRNA. In one embodiment, a "1" indicates the biological data associated with the matrix element (e.g., which column is being looked at) and a "0" indicates no association.

In one embodiment, non-binary relationships may be used. For instance, a value of the free energy of interaction could be used itself or a value of the significance of the biological data corresponding to the matrix element. The actual form for a correlation matrix may be as a classic matrix, or may be a set of linked lists. Essentially, the data may be stored in any form. Additionally, only the "1" values may need to be stored and "0" values may be inferred.

In FIG. 9B, the columns 960 of matrix 950 correspond to GO terms. These GO terms 960 may be shared by several of the target nucleic acids, e.g., sets 970 of genes. Thus, if a microRNA interacts with any of the genes that are linked to a GO term, then that GO term is associated with that microRNA and the matrix element is "1". If a microRNA does not interact with any of the genes that are linked to a GO term, then that GO term is not associated with that microRNA and the matrix element is "1".

E. Creating a Distance Matrix Based on the Correlation Matrix (Block 230)

The correlation matrix may be used to determine a distance between the miRNA. The values of "0" and "1" may be used a multi-dimensional position and thus a distance may be calculated. In one aspect, this distance may be viewed as a functional distance. Thus, in one embodiment, a functional distance is calculated between each pair of microRNAs according to the composition with respect to common GO-significant terms. Each dimension or direction of the matrix would be a different piece of biological data, or different Go term.

The definition (formula) for the distance may be any variety. It may be a strict Euclidean distance that includes a square root of the sum of the squares of the difference in position for each dimension between each miRNA. The distance may also be a weighted Euclidean distance and even curvilinear or non-orthogonal directions may be assumed between the biological data.

In one embodiment, the functional distance matrix is constructed according to a method based on a similarity distance calculation that is conventional in the field, called "Czekanowski-Dice" (Kimura M., 1980). Other methods for calculating distance can be used, such as, for example, the method of Kimura (Kimura M., 1980).

F. Clustering First Nucleic Acids (Block 240)

Figure 6:
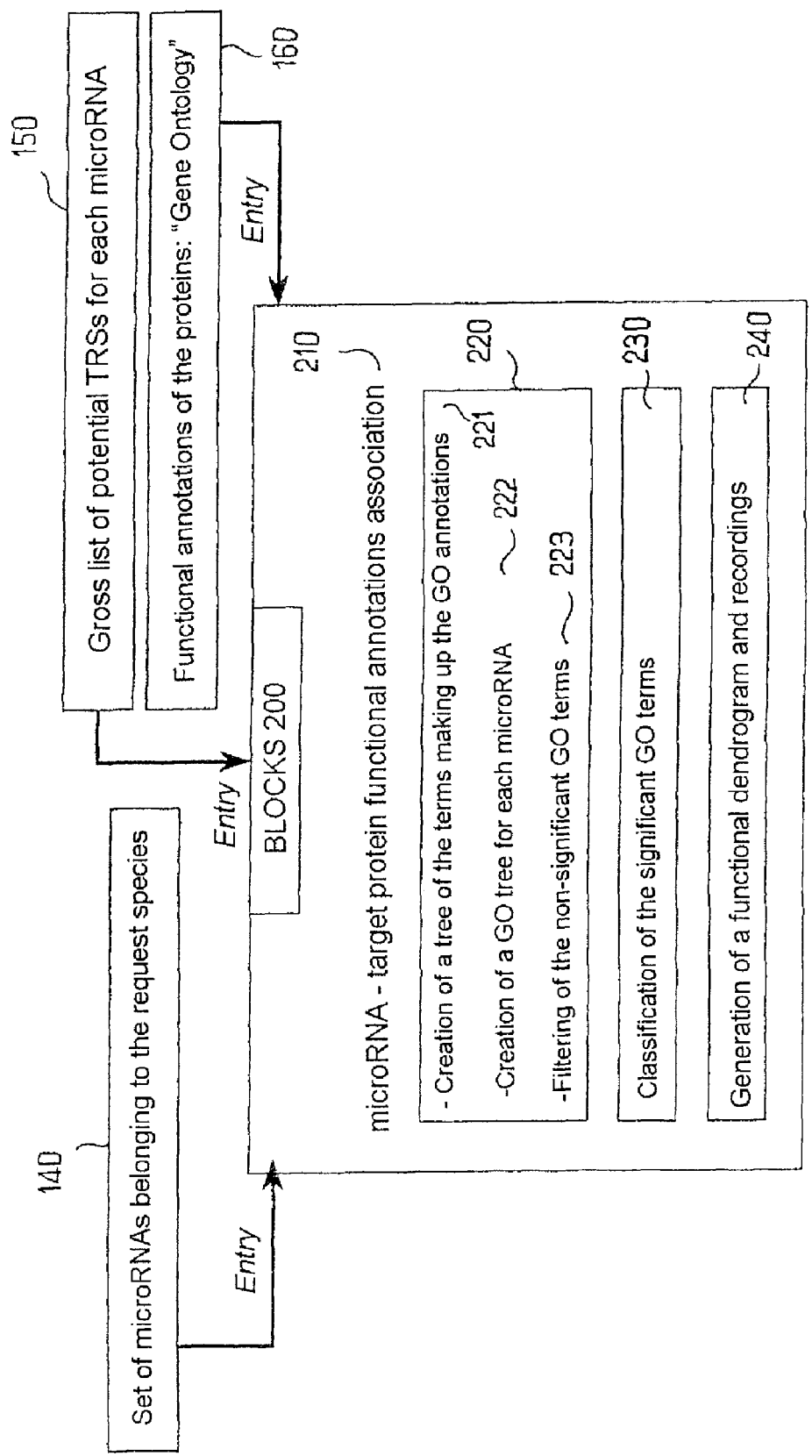
FIG. 6 illustrates schematically the functional clustering of nucleic acids according to an embodiment of the present invention.

In the fourth subblock 240 in FIG. 6, the distance matrix is used to cluster miRNA. In one aspect, a dendrogram of the functional relationships between the microRNAs is created from the distance matrix generated by the subblock 230, and the dendrogram is recorded in a file that is here called "dendrogram". Other structures besides a dendrogram may be created from the clustering, although a dendrogram is the most common. In one aspect, the clusters produced are only those which will have the largest set of information in common among each of the first nucleic acids (e.g., miRNA) of the cluster.

Since the biological data, which is associated with each miRNA, can vary, the clustering of the first nucleic acids (miRNA) can be based on many different attributes or characteristics of the target nucleic acids (mRNA). Thus, the clustering can be based on which mRNA the miRNA interact, which was determined by methods from section A. In other embodiments, the functional clustering can be made based on the GO terms which are associated to the genes. In this case, the clustering is independent of the name of the gene. Of course, other embodiments may cluster based on any other biological data linked to the target nucleic acids.

In one embodiment, a method of the WPGMA (acronym for "Weighted Pair Group Method with Arithmetic mean") type is used to perform the clustering. Other methods include the UPGMA method (Unweight Pair Group Method with Arithmetic mean), or the method known as "Neighbour Joining". Additionally, methods that do not directly use pairwise distances may also be used. For example, under maximum parsimony, the preferred phylogenetic tree is the tree that requires the least number of evolutionary changes, or under maximum likelihood is the most likely tree based on experimental data. In such an example, pairwise distances are still used to provide a measure of the scoring or probability that determines the best clustering.

Figure 10:
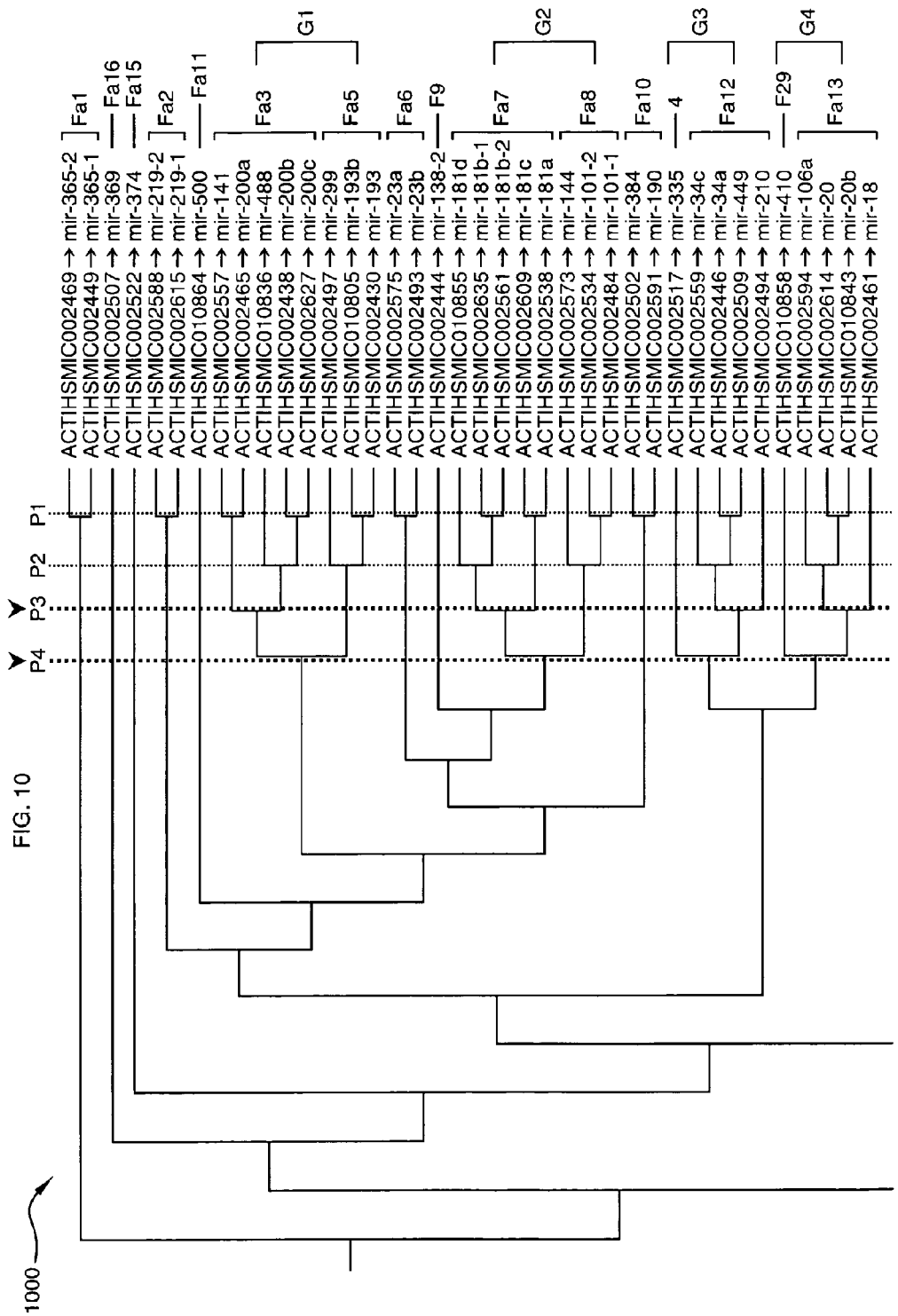
FIG. 10 illustrates a dendrogram generated in accordance with an embodiment of the present invention.

FIG. 10 illustrates a dendrogram 1000 generated in accordance with an embodiment of the present invention. Dendrogram 1000 represents the functional relationships between the microRNAs. Several levels of depth can be defined. In particular, these levels depend on the functional distance that separates the microRNAs. For example, the set of microRNAs having a branching node at a depth 3 (P3) can be referred to as "functional family" (Fa). Similarly, the set of microRNAs having a branching point at the depth 4 (P4) can be referred to as "functional group" (G).

Naturally, such a method for selecting the functional families and/or functional groups may be different according to the method for constructing the tree. In all cases, the method according to the preferred embodiment of the invention thus makes it possible to decipher a microRNA code on the basis of the functional families and groups obtained.

Byway of example, it is seen, according to FIG. 10, that the mir365-2 and mir365-1 microRNAs cooperate to regulate the function F1 linked to the family Fa1. It is also seen that two families Fa3 and Fa5 comprising two sets of microRNAs form a group G1. In this group, the microRNAs are associated with biological phenomena illustrated by the functions F3 and F5 which have been determined as having a link with one another. In order to further enhance the information provided at this stage, the method can include post-processing of the information provided in particular by the dendrogram is carried out.

In other embodiments, the level of depth may not be the determining factor for identifying a cluster of miRNA that have functional relatedness. Instead a percentage of a normalized distance, the normalized distance itself, or even a raw distance could be used as a threshold for identifying clusters. Such a percentage could be used as a threshold value such that miRNA are organized into a cluster if greater than 25% of the total target genes or mRNA (or other biological data) of the cluster are shared among the miRNA of the cluster. Equivalently, in a Venn diagram perspective, the shared microRNA may be viewed as the intersection of the sets of target genes associated with each miRNA.

For instance for 3 miRNAs, they are clustered together if among their target genes, at least 25% of these genes are targeted by the 3 miRNAs. In one aspect, a single calculation is done with where the percentage is the shared number of target genes divided by the total number of target genes associated with the miRNAs of the cluster. Alternatively, the percentage could be based on the number of genes for each miRNA that are shared. For instance for 3 miRNAs, 25% of the target genes for a particular miRNA must be shared by the other miRNA of the cluster. In one aspect, three percentages are calculated with each one being greater than the predetermined amount, e.g., 25%, where each percentage is the shared target genes divided by the total target genes associated with a particular miRNA.

Figure 11:
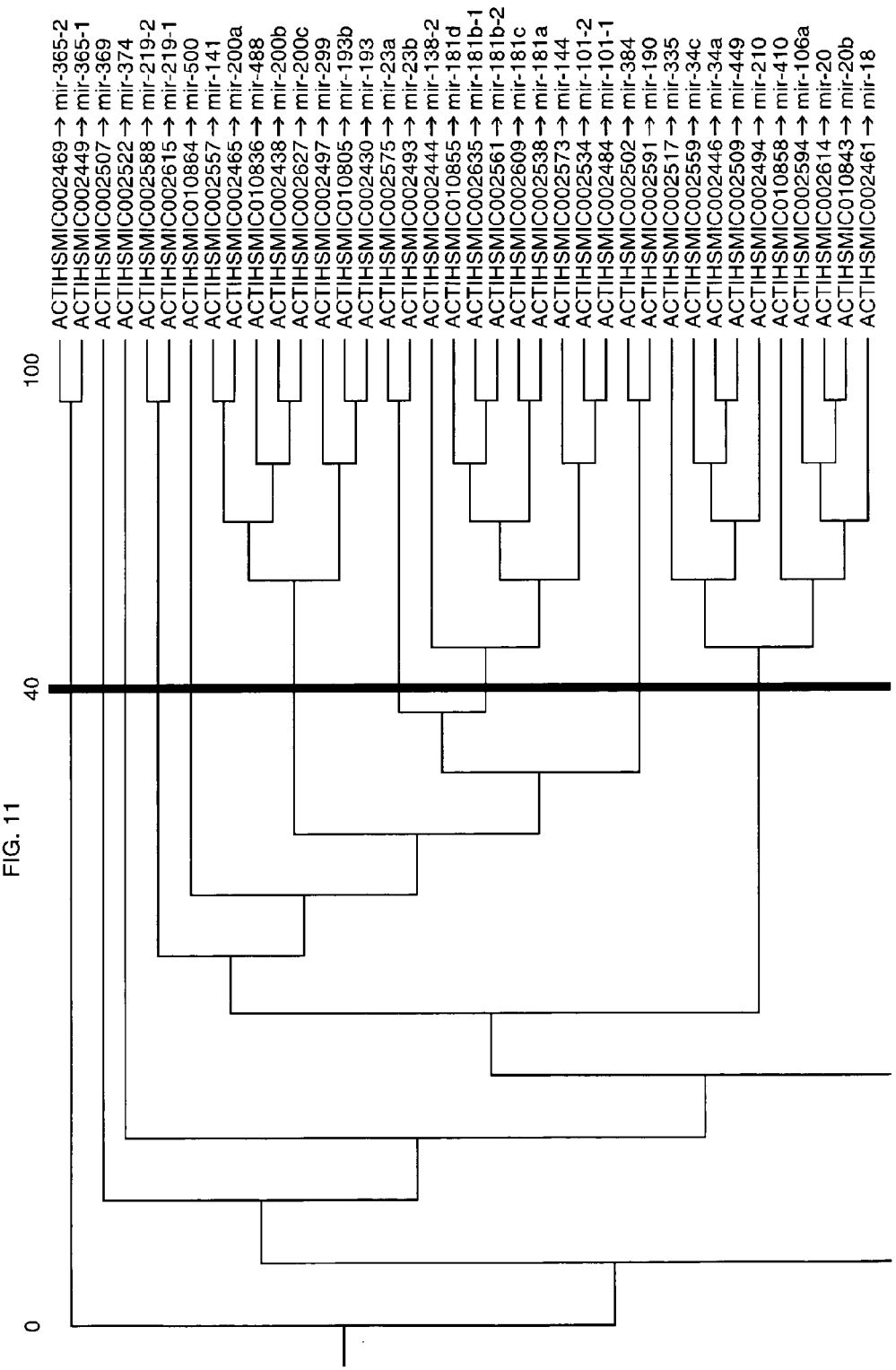
FIG. 11 illustrates a dendrogram with the distance between connected miRNA being signified with a percentage, or normalized distance, according to an embodiment of the present invention.

FIG. 11 illustrates a dendrogram with the distance between connected miRNA being signified with a percentage, or essentially a normalized distance. In this example, the 40% marker was used to signify that all connected miRNA at that level or higher may be organized into functionally-related sets (microRNA code). This is only one example of how the cutoff value may be chosen within the dendrogram to identify clusters according to specific biological problems. By moving left and right the cutoff, one can respectively zoom-out and zoom-in in the functional relationships between the microRNAs analyzed.

G. Assigning Biological Functions to Nucleic Acids of a Cluster

Once a cluster has been identified, certain biological functions may be assigned to the miRNA of the cluster. The biological functions may be determined from the biological data associated with the miRNA of the cluster. The linkage between the biological functions and the biological data may be an identity. For example, the biological functions may be the GO annotations that make up the biological data, or essentially the biological phenomenon associated with the annotations. In embodiments where the biological data corresponds to the target nucleic acids, the biological functions may be the regulation of specific target nucleic acids by a miRNA of the cluster.

Certain biological functions that have been identified as being linked to the biological data of a cluster may then be assigned to the cluster, and therefore assigned to the miRNA of the cluster. In one embodiment, biological functions linked to only the biological data common to all of the miRNA of a cluster are assigned to the miRNA of the cluster. Thus, only the functional annotations that are common to all of the miRNA of the cluster are assigned to the miRNA of the cluster. The miRNA of the cluster may then be viewed as miRNA code for these shared biological functions.

In one embodiment, the functionality of regulating the target nucleic acids that are shared among the miRNA of the group are assigned to the cluster. Accordingly, in this embodiment, the target nucleic acids (e.g., mRNA) that are shared by the miRNA are identified as true targets of the miRNA. Accordingly, embodiments make it possible to select the corresponding potential target recognition sequences (TRSs). Advantageously, only 20 to 50 significant targets per microRNA are identified by virtue of an embodiment of the invention.

In other embodiments, the common biological data can be identified. The target nucleic acids that are linked to any of the common biological data can also be identified. These targets may then be identified as being the true targets of the miRNA in the cluster, and the biological function of regulating these targets may be assigned to the miRNA of the cluster. Alternatively, only target nucleic acids that are linked to a predetermined number or percentage of the common biological data are considered as true targets.

The non-common biological data may still be stored and associated to the microRNA as it may be useful for other clusters. With further analysis, this non-common biological data may be used to determine if there exists other functional links between the microRNA of different set, subsets, clusters, or subsets of clusters.

IV. Visualizing Results

In a post-processing step, methods of exploration, evaluation, analysis and interpretation of the results derived from method 200, in particular of the results contained in the "dendrogram" file, are, inter alia, carried out. To this effect, interactive visualization interfaces and dedicated navigators can be used. In this manner, a simple, intuitive and interactive extraction and presentation of the information and results contained in the "microRNA-possibleTRSs-GO_functional_annotations-significant" (enhanced gross list) list is made possible.

More specifically, a display for visualization of the target genes and of the potential sequences for target recognition (TRSs) by microRNAs and/or, for example, by functional families of microRNAs can be used. It is also possible to use a display for visualization of the GO terms that are associated with the microRNAs selected individually and/or selected by functional families and/or selected by functional groups. Such a display can be effected by means of: biological functions of the microRNA-possible-TRSs associated data; molecular functions of the microRNA-possible-TRSs associated data; and cellular compartments in which the microRNA-possibleTRSs associations function.

Using the above or other displays, one may gain access to various pieces of information such as: the target genes for these microRNAs and potential target recognition sequences (TRSs); details on the interactions between the microRNAs and their potential target recognition sequences (TRSs), for an evaluation of these interactions; and pathologies related to the microRNA-possible-TRSs associated data.

In order to achieve such aims, filtering functions may be implemented for displaying the information and the results contained in the "microRNA-possibleTRSs-GO_functional_annotations-significant" list. An algorithm based on set theory can be used so as to visualize, for the sets of microRNAs sharing a set of GO terms in common ("functional families" and/or "functional groups" of microRNAs), the set of GO terms of each of these microRNAs, and/or those shared by all or by one subset of the microRNAs of this microRNA set.

Key parameters that may be modified in this algorithm are, in particular: the depth in the dendrogram for visualizing either functional groups or functional families; and the number of microRNAs (as %, for example) that must share common GO terms. Other parameters and criteria mentioned herein and known by those skilled in the art may be used. Such parameters makes it possible to obtain the GO terms specific for each of the microRNAs of the functional group or of the functional family analyzed.

Moreover, steps which allow navigation in the GO_significant tree are implemented in order to locate and identify in this tree the parent-child relationships between GO terms associated with a microRNA, with a subset or with the set of microRNAs belonging to a functional family or functional group.

EXAMPLES

The following examples are offered to illustrate, but not to limit the claimed invention.

An example of an application of the invention will now be described in the context of the deciphering of a microRNA code in humans. In particular, an embodiment of the invention presented above was applied to 239 human microRNAs that are conserved with mouse. These 239 microRNA, or any other set of microRNA, may be determined by methods known in the art. The results derived from this example were validated by an overlap with known and published results. More specifically, validations were made with known experimental results, and a verification of the coherence of the results with current knowledge on microRNAs was obtained.

First results of the application of the invention to 239 human microRNAs have been represented in a table 1 in FIG. 12. As can be seen, the method results in the identification of 89 functional families (F1 to F89). These families correspond to groups of microRNAs having a branching node at depth 3 of the dendrogram 1000. In table 1, the microRNAs between parentheses correspond to paralogs.

1. Functional Families Containing at Least 2 microRNAs

MicroRNAs of which the sequences do not exhibit any similarity were able to be clustered together and shown to participate synergistically and in a coordinated manner in the regulation of the same biological function. In table 1 of FIG. 12, 57 families comprising 2 members or more were identified.

2. Orphan Functional Families

The method of the invention also makes it possible to identi families containing only one microRNA, hereinafter referred to as orphan families. These microRNAs encode functions that are not significantly shared by other microRNAs or functional families of microRNAs. In table 1 of FIG. 12, the method made it possible to identify 32 orphan families, shown in FIG. 13. They correspond either to microRNAs that have an individual method of function, or to functional families that are incomplete due to very partial knowledge of the complete set of microRNAs.

3. Functional Groups of microRNAs

According to the table of FIG. 14, 36 functional families defined at depth 3 (P3) of the dendrogram are grouped together in 18 functional groups identified as from G1 to G18 at depth 4 (P4) of the dendrogram. These functional groups of microRNAs reveal functional cross interactions required within the network defined by the microRNA code so as to co-regulate different functions in a synergy necessary for cell and tissue function in organisms.

4. Validation by Analysis of the Groups of Paralogous microRNAs

As illustrated in FIG. 15, paralogous microRNAs with high sequence similarity (e.g., 90%-100%) were naturally clustered in the same functional family or group by embodiments of the invention which do not take into account sequence similarity. Thus, the paralogous microRNAs, for which the sequence similarity suggests that they should be clustered together, were indeed clustered together. In humans, 42 functional groups of microRNAs are considered to be paralogous, i.e. copies of the same microRNA.

Although embodiments cluster together microRNAs with high sequence similarity, microRNAs with lower sequence similarity (e.g., below 80%) may also be clustered together. For example, an embodiment of the invention classifies 34 of these 42 groups of paralogous microRNAs into 34 different functional families, despite sequence variations that are sometimes considerable (for example, 29.2% differences, i.e. 7 nucleotides different out of 24, in the case of the two paralogs mir-193 and mir-193b).

Furthermore, as illustrated in FIG. 16, for 8 groups of paralogous microRNAs, it is shown that relatively small sequence differences can also result in substantial functional differences between each paralog of a group, while sometimes the differences do not. In particular, three cases can be differentiated in this table. The case of the mir-302 paralogs: the 4 microRNAs of this group of paralogs belong to two different functional families F55 and F56, which belong to the same functional group G13. This means in particular that the functional differences within this group of paralogs are relatively minor. The two families act in a coordinated manner on functions that act in strict synergy.

In the case of the Let-7 paralogs, the microRNAs are distributed in three functional families. Two of them, F27 and F28, belong to the same functional group G6 (depth 4 of the dendrogram). The third family, F30, which contains Let-7d, does not belong to this functional group. However, a dendrogram analysis shows that the family F30 has a common node at depth 5 with the functional group G6, suggesting that the set of members of the group of Let-7 paralogs act in a coordinated manner on functions that act in synergy in cells and tissues.

The microRNA of a group of paralogs can also have different functions. The members of the other 6 groups of paralogs, in FIG. 16, have different functions. Particularly, with regards to mir-34b, this microRNA has an additional nucleotide in the 5' position. The result of this difference is that the nucleus is different from the other members of this group of paralogs, and therefore the difference in targets and function.

5. Validation by Analysis of the microRNAs Involved in the Same Function

An embodiment of the invention classified in the same family, or functional group, the only two groups of microRNAs which are known to be involved in the same function. This makes it possible to demonstrate, in particular, that miR-15 and miR-16 are both involved in leukemias of "B cell chronic lymphocytic leukemia" type (Calin et al., 2002; Calin et al., 2004). These two microRNAs have at least one target nucleic acid in common, the Bcl2 gene (Cimmino et al., 2005).

Although the two microRNAs have no sequence similarity, the method of the invention groups together in the same functional family the mir16-1, mir-16-2 and mir15b microRNAs. In addition, in the case of the microRNAs of the Let-7 family, 10 members of this family of 11 microRNAs are grouped together by the invention into the same functional group.

6. Functional Profile of the microRNAs

An embodiment of the invention helps to establish a specific functional profile of each microRNA or family of microRNAs and also functional relationships that exist between these families when they belong to the same functional group. The term "functional profile" is intended to mean a set of functions or, in an equivalent manner, a set of biological phenomena. For each microRNA, the functions in which a microRNA code co-regulate in a coordinated manner or synergy with the other members of their functional family are attributed.

All these results may be integrated into a file that has various fields such as the following: Family, ACTINAME, microRNA, GO, and GO:Accession. Family denotes the identification of the functional family. ACTINAME is an identification of the microRNA specific to the invention. MicroRNA denotes the standard identification of the microRNA. GO denotes the set of GO terms associated with a microRNA is listed in this field. GO:Accession denotes codes denoting each of the GO terms are listed in this field. The post-processing of the method makes it possible to exploit the data included in this file.

For example, post-processing can provide the list of "GO" terms associated with mir-34a, i.e.: actin binding, aminoglycan biosynthesis, apoptosis, ATP binding, ATP synthesis coupled proton transport, ATPase activity, coupled, binding, biological_process unknown, calcium ion binding, catalytic activity, cell adhesion, cell proliferation, cellular_component unknown, cytochrome-b5 reductase activity, cytokinesis, cytoplasm, cytoskeleton, development, DNA binding, DNA-directed RNA polymerase activity, electron transport, endocytosis, endoplasmic reticulum, epsilon DNA polymerase activity, G-protein coupled receptor protein signaling pathway, G-protein signaling, coupled to cyclic nucleotide second messenger, G1/S transition of mitotic cell cycle, glycosphingolipid biosynthesis, Golgi apparatus, GTP binding, heme binding, humoral defense mechanism (sensu Vertebrata), hydrogen-translocating V-type ATPase complex, hydrolase activity, integral to membrane, integral to plasma membrane, intracellular, intracellular protein transport, intracellular signaling cascade, ion transport, kinase activity, ligase activity, magnesium ion binding, membrane, membrane fraction, microtubule associated complex, mitotic metaphase plate congression, molecular_function unknown, morphogenesis, muscle development, neurogenesis, neuropeptide signaling pathway, nuclear mRNA splicing, via spliceosome, nucleic acid binding, nucleus, organelle organization and biogenesis, oxidoreductase activity, oxygen transport, phosphoprotein phosphatase activity, positive regulation of I-kappaB kinase/NF-kappaB cascade, protein amino acid glycosylation, protein amino acid phosphorylation, protein binding, protein folding, protein modification, protein phosphatase type 2A complex, protein phosphatase type 2A regulator activity, protein serine/threonine kinase activity, protein ubiquitination, protein-tyrosine kinase activity, proteolysis and peptidolysis, proton transport, receptor activity, redox signal response, regulation of cell cycle, regulation of mitotic metaphase/anaphase transition, regulation of transcription from Pol II promoter, regulation of transcription, DNA-dependent, regulation of translational initiation, rhodopsin-like receptor activity, RNA binding, RNA polymerase II transcription factor activity, signal transducer activity, signal transduction, small GTPase mediated signal transduction, structural molecule activity, transcription coactivator activity, transcription factor activity, transcription from Pol II promoter, transferase activity, translation initiation factor activity, transmembrane receptor protein tyrosine phosphatase activity, transport, transporter activity, ubiquitin cycle, ubiquitin ligase complex, ubiquitin-protein ligase activity, voltage-gated calcium channel activity, zinc ion binding.

7. Functional Profile of the "Functional Families" of microRNAs

In an example of the functional family F12 containing mir-34a, an embodiment of the method finds 45 GO terms (60.7%) in common in the F12 family, i.e.: actin binding, ATP binding, binding, biological_process unknown, calcium ion binding, cell adhesion, cellular_component unknown, cytoplasm, cytoskeleton, development, DNA binding, G-protein coupled receptor, Golgi apparatus, GTP binding, hydrolase activity, integral to membrane, integral to plasma membrane, intracellular protein transport, intracellular signaling cascade, kinase activity, magnesium ion binding, membrane, membrane fraction, molecular_function unknown, muscle development, neurogenesis, nucleic acid binding, nucleus protein binding, protein serine/threonine kinase activity, protein ubiquitination receptor activity, regulation of cell cycle, regulation of transcription DNA-dependent, rhodopsin-like receptor activity, RNA binding, signal transduction transcription, coactivator activity, transcription factor activity, transcription from Pol II promoter, transferase activity, transport, ubiquitin cycle, ubiquitin, ligase complex, ubiquitin-protein ligase activity, zinc ion binding.

The post-processing makes it possible to select the GO terms present in the set or a subset of the microRNAs of such a functional family or of a functional group. It also makes it possible to visualize, on a GO tree, the terms selected as a function of parameters used, as well as identify the major function(s) in which the microRNAs of the functional family or of the functional group considered are involved.

8. Identification of the microRNA Target Genes

Based on the above displays and the functional annotations, the corresponding potential target recognition sequences (TRSs) may be selected. Advantageously, only 20 to 50 significant targets per microRNA are identified by virtue of an embodiment of the invention.

9. Validation by Analysis of the Known microRNA Targets in Humans

In the final list of biologically significant target recognition sequences, two validated targets are found in humans. The NRAS gene, which is a validated target for the Let-7 microRNAs in humans (Cimmino et al., 2005), is in particular found. The BCL2 gene, which is a validated target for the mir-15 and mir-16 microRNAs in humans (Johnson et al., 2005), is also found.

10. MicroRNA Associations and Pathologies

For each microRNA, the pathologies in which they are liable to play a role were associated. Three exemplary methods were used to carry out this association: the microRNA is harbored by a gene which is itself associated with a pathology; the microRNA targets a gene associated with a pathology; and the microRNA is located in a chromosomal region associated with one or more pathologies.

In particular, the invention is applicable to another species, regardless of the method for identifying the microRNAs, i.e. either direct or by sequence homology with another species. Moreover, it is applicable to another species provided that sequences of the genes encoding proteins for this species are known. For example, the invention can be applied to mice, rats, dogs or chimpanzees.

In addition, as mentioned above, it can be generalized to any family of nucleic acids that interact with target molecules and function as a network in a cooperative manner. This is in particular the case of classes of non-coding RNAs that do not belong to the microRNA family or class. In this regard, mention may be made of the snoRNA class, which consists of hundreds of molecules that are known to act by base complementarity with their target. To date, a set of approximately 200 molecules belonging to two subclasses that differ by virtue of their structural characteristics (CD snoRNAs and H-ACA snoRNAs) and act in synergy on ribosome biogenesis, has been identified. However, a large number of molecules belonging to these two classes are orphan molecules, i.e. it has not yet been possible to identify their target and their function is therefore unknown.

Moreover, as will have been understood, the method of the invention makes it possible to integrate, into an enhanced gross list, new microRNAs that will be identified over time. Specifically, at least 800 remain to be discovered in humans and mammals. Such an integration of new microRNAs as they are discovered makes it possible to achieve many goals.

For example, one may complete the functional families already identified and presented in this document. This is in particular the case of the "orphan" families that contain only one microRNA. One may refine the quality of the prediction of their function by increasing the accuracy of the prediction, for example by modifying the list of functions assigned to the microRNAs or the composition of the families. One can bring about the creation of new functional families that have not yet been detected. Also, functional families identified by the invention and presented in this document may be subdivided or grouped together or modified, and thus for the functions predicted to date to be refined.

REFERENCES

Ashburner et al. Nature Genet. 25: 25-29 (2000).
Bartel P., Cell, 116, 281-297, 2004.
Baskerville et al., RNA., March; 11(3):241-7, 2005.
Brennecke et al., Cell., 113(1):25-36, 2003.
Brennecke et al., PLoS Biol., March; 3(3):e85, 2005.
Burgler et al., BMC Genomics., June 8; 6(1):88, 2005.
Calin et al., Proc. Natl. Acad. Sci., USA, 26; 99(24):15524-9, 2002.
Calin et al., Proc. Natl. Acad. Sci., USA, 10; 101(32):11755-60, 2004.
Calin et al., "Proc Natl Acad Sci USA. 2; 101(9): 2999-3004 (2004).
Chen et al., Science, 303(5654):83-6, 2004.
Cimmino et al., Proc. Natl. Acad. Sci. USA. 2005 Sep. 27; 102(39): 13944-9.
Doench et al., Genes Dev., March 1; 18(5):504-11, Epub, Mar. 10, 2004.
Dostie et al., RNA. 9(2): 180-6. (2003). Erratum in: RNA. 9(5): 631-2 (2003).
Enright et al., Genome Biol., 5(1):R1, 2003.
Esau et al., J Biol Chem., 10; 279(50):52361-5, 2004.
Grun D. et al., PLoS Comput Biol., June; 1(1):e13, 2005.
He L. et al., Nat Rev Genet., 5(7):522-31, Review, 2004.
He L. et al., Nature, June 9; 435(7043):828-33, 2005.
Hobert O, Trends Biochem Sci. 2004 September; 29(9): 462-8. Review.
Houbaviy et al., Dev Cell. 5(2):351-8, 2003.
Hubbard et al., Nucleic Acids Res. 2005 Jan. 1; 33 Database issue: D447-D453.
John B. et al. PLoS Biol. 2004 November; 2(11): e363. Epub 2004 Oct. 5.
Johnson et al., Cell. 2005 Mar. 11; 120(5): 635-47.
Kasashima K et al., Biochem Biophys Res Commun. 17; 322(2): 403-10 (2004).
Kawasaki H. et al., Nature. 2003 Jun. 19; 423(6942): 838-42.
Kim J. et al., Proc Natl Acad Sci USA. 6; 101(1): 360-5 (2004).
Kimura M., Journal of Molecular Evolution 16: 111-120 (1980).
Kiriakidou et al., Genes Dev., May 15; 18(10):1165-78, 2004.
Krek et al., Nat Genet, May; 37(5):495-500, 2005.
Krichevsky et al., RNA, 9(10):1274-81, 2003.
Kuwabara, Cell., 19; 116(6):779-93, 2004.
Lai et al., Nat Genet., April; 30(4):363-4, 2002.
Lewis et al., Cell., January 14; 120(1):15-20, 2005.
Lewis et al., Cell., December 26; 115(7):787-98, 2003.
Lim et al., Nature, 30, 2005.
Lu et al., Nature, June 9; 435(7043):834-8 2005.
Mattick et al., Bioessays, 25(10):930-9, 2003.
Metzler et al., Genes Chromosomes Cancer, 39(2):167-9, 2004.
Michael et al., Mol Cancer Res., 1(12):882-91, 2003.
Miska et al., Genome Biol., 5(9):R68, 2004.
Muller-Tidow et al., Lung Cancer, 45 Suppl 2:S145-50, 2004.
O'Donnell et al., Nature, June 9; 435(7043):839-43, 2005.
Poy et al., Nature, 11; 432(7014):226-30, 2004.
Rehmsmeier et al., RNA, October; 10(10):1507-17, 2004.
Reinhart et al., Nature, 403(6772):901-6, 2000.
Sempere et al., Genome Biol., 5(3):R13, 2004.
Stark et al., PLoS Biol., December; 1(3):E60, 2003.
Steinberg D, The Scientist 19(12): 14-16 (2005).
Takamizawa J. et al., Cancer Res., 1; 64(11):3753-6, 2004.
Xie X. et al., Nature. 2005 Mar. 17; 434(7031): 338-45.
Xu P. et al., Trends Genet. 20(12): 617-24 (2004).
Yekta S. et al., Science. 23; 304 (5670): 594-6 (2004).
Yoon S. et al., Bioinformatics 1-8 (2005).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A method of analyzing a plurality of first nucleic acids that can interact with at least one target portion of respective target nucleic acids to identify at least one cluster of the first nucleic acids that potentially cooperate with one another so as to affect one or more biological functions, the method comprising:
   for each of the first nucleic acids, determining whether that first nucleic acid respectively interacts with each of the target nucleic acids, wherein the first nucleic acids and the target nucleic acids are from different nucleic acid families;
   for each interaction, identifying one or more biological data that are linked to the target nucleic acid of that interaction;
   for each of the first nucleic acids, associating, with that first nucleic acid, at least a portion of the biological data linked to the target nucleic acids with which that first nucleic acid interacts;
   creating, with a programmed computer system, a correlation matrix that indicates whether each of the identified biological data is associated with each of the first nucleic acids, wherein the identified biological data is a plurality of biological data, and wherein the correlation matrix provides a multi-dimensional position for each first nucleic acid, each dimension corresponding to a different one of the plurality of biological data;
   creating, with the programmed computer system, a distance matrix by calculating a distance between a multi-dimensional position of one first nucleic acid and a multi-dimensional position of another first nucleic acid for each pair of the first nucleic acids, wherein calculating a distance for a pair of the first nucleic acids includes:
      taking a difference between the positions for each dimension of the multi-dimensional positions of the first nucleic acids of the pair; and
      calculating a sum of the differences to obtain the distance for the pair;
   clustering, with the programmed computer system, the first nucleic acids based on the distances between the pairs of first nucleic acids in the distance matrix;
   linking a set of biological functions with the biological data associated with the first nucleic acids of a cluster; and
   assigning to the first nucleic acids of the cluster at least a portion of the linked biological functions.

2. The method of claim 1, wherein a plurality of biological functions are assigned to the first nucleic acids of the cluster, and wherein the at least a portion of the linked biological functions assigned to the first nucleic acids of the cluster correspond to biological data that is shared by the first nucleic acids of the cluster.

3. The method of claim 2, further comprising:
   identifying the target nucleic acids linked with the shared biological data as true targets of the first nucleic acids of the cluster.

4. The method of claim 1 wherein the first nucleic acids and the target nucleic acids are each from an RNA nucleic acid family, wherein the first nucleic acids are microRNA and the target nucleic acids are messenger RNA, and wherein the target portions are in a 3'UTR region of the messenger RNA.

5. The method of claim 1 wherein the biological data is a name of a respective target nucleic acid or includes functional annotations.

6. The method of claim 1 wherein clustering the first nucleic acid includes creating a dendrogram.

7. The method of claim 1 wherein clustering the first nucleic acids comprises:
calculating a first amount of biological data shared by a set of the first nucleic acids, the set being determined based on the distances between first nucleic acids; and
creating a cluster of the first nucleic acids of the set if the first amount is at least a predetermined amount.

8. The method of claim 7 wherein the predetermined amount is a percentage based on a total number of biological data associated with the first nucleic acids of the cluster.

9. The method of claim 1 wherein clustering the first nucleic acids comprises:
identifying a depth related to a set of first nucleic acids; and
creating a cluster if the depth is below a predetermined value.

10. The method of claim 1 wherein defining a distance includes taking a difference between corresponding correlation matrix elements for each of the biological data of the first nucleic acids of a pair.

11. The method of claim 1, further comprising:
creating a complete list of all of the biological data linked to the target nucleic acid of the interactions;
for each first nucleic acid, creating a specific list of the biological data linked to the target nucleic acid with which that first nucleic acid interacts,
wherein associating, with a first nucleic acid, at least a portion of the biological data linked to the target nucleic acids with which that first nucleic acid interacts includes:
comparing the specific list for the first nucleic acid to the complete list to determine the at least a portion of the biological data to associate with the first nucleic acid.

12. The method of claim 11 wherein comparing includes using a statistical method to calculate a significance value of each of the biological data in the specific list, and wherein only biological data having a significance value within a predetermined range is included in the at least a portion of the biological data associated with the first nucleic acid.

13. The method of claim 1 wherein determining whether that first nucleic acid respectively interacts with each of the target nucleic acids comprises:
identifying in the target portion of the target nucleic acid:
a first zone in which no break in complementarity with the first molecule (M) is permitted; and
adjacent to the first zone, a second zone in which one or more breaks in complementarity with the first nucleic acid are permitted; and
determining an energy of interaction of the first and second zones.

14. The method of claim 13 wherein the first zone in the target portion corresponds to a spatially extended nucleus (Nu).

15. A computer program product comprising a non-transitory computer readable medium encoded with program code for controlling operation of a computer system to analyze a plurality of first nucleic acids that can interact with at least one target portion of respective target nucleic acids to identify at least one cluster of the first nucleic acids that potentially cooperate with one another so as to affect one or more biological functions, the program code including:
program code for determining, for each of the first nucleic acids, whether that first nucleic acid respectively interacts with each of the target nucleic acids, wherein the first nucleic acids and the target nucleic acids are from different nucleic acid families;
program code for identifying, for each interaction, one or more biological data that are linked to the target nucleic acid of that interaction;
program code for associating, with each of the first nucleic acids, at least a portion of the biological data linked to the target nucleic acids with which that first nucleic acid interacts;
program code for creating a correlation matrix that indicates whether each of the identified biological data is associated with each of the first nucleic acids, wherein the identified biological data is a plurality of biological data, and wherein the correlation matrix provides a multi-dimensional position for each first nucleic acid, each dimension corresponding to a different one of the plurality of biological data;
program code for creating a distance matrix by calculating a distance between a multi-dimensional position of one first nucleic acid and a multi-dimensional position of another first nucleic acid for each pair of the first nucleic acids, wherein calculating a distance for a pair of the first nucleic acids includes:
taking a difference between the positions for each dimension of the multi-dimensional positions of the first nucleic acids of the pair; and
calculating a sum of the differences to obtain the distance for the pair;
program code for clustering the first nucleic acids based on the distances between the pairs of first nucleic acids in the distance matrix;
program code for linking a set of biological functions with the biological data associated with the first nucleic acids of a cluster; and
program code for assigning to the first nucleic acids of the cluster at least a portion of the biological functions.

16. The method of claim 1 wherein the biological functions define with which target nucleic acids the first nucleic acids of the cluster interact.

17. The method of claim 1 wherein the biological data associated with the first nucleic acids of the cluster includes the set of biological functions.

18. The method of claim 1 wherein a "0" value of a correlation matrix element indicates that specific biological data is not associated with a specific first nucleic acid, and wherein a "1" value of the correlation matrix element indicates that the specific biological data is associated with the specific first nucleic acid.

19. The method of claim 1 wherein a correlation matrix element indicates a degree that biological data is associated with each of the first nucleic acids.

20. The method of claim 10, wherein defining a distance further includes summing a function of each of the differences.

21. The method of claim 1 wherein the distance is based on a similarity distance calculation.

22. The method of claim 11 wherein the complete list and the specific lists of the biological data linked to the target nucleic acid with which that first nucleic acid interacts are relational trees.

23. The method of claim 12 wherein the statistical method is based on a hypergeometric distribution.

24. The method of claim 1 wherein clustering includes using a weighted pair group method with arithmetic mean (WPGMA).

25. The method of claim 1, wherein the correlation matrix provides a multi-dimensional position for each first nucleic acid, each dimension corresponding to a different one of the plurality of biological data, and wherein creating the distance matrix includes:
for each pair of the first nucleic acids:
calculating the distance between a multi-dimensional position of one first nucleic acid and a multi-dimensional position of another first nucleic acid.

26. The method of claim 25, wherein calculating the distance for a pair of the first nucleic acids includes:
taking a difference between the positions for each dimension of the multi-dimensional positions of the first nucleic acids of the pair; and
calculating a sum of the differences to obtain the distance for the pair.

27. The method of claim 2, wherein a plurality of biological functions are assigned to the cluster.

28. The method of claim 3, wherein only a portion of the linked biological functions are assigned to the cluster.

29. The method of claim 7, wherein the predetermined amount is greater than one.

30. The computer program product of claim 15, wherein a plurality of biological functions are assigned to the first nucleic acids of the cluster, and wherein the at least a portion of the linked biological functions assigned to the first nucleic acids of the cluster correspond to biological data that is shared by the first nucleic acids of the cluster, and wherein the program code further includes:
program code for identifying the target nucleic acids linked with the shared biological data as true targets of the first nucleic acids of the cluster.

31. The computer program product of claim 15 wherein the program code for clustering the first nucleic acids includes:
program code for calculating a first amount of biological data shared by a set of the first nucleic acids, the set being determined based on the distances between first nucleic acids; and
program code for creating a cluster of the first nucleic acids of the set if the first amount is at least a predetermined amount.

32. The computer program product of claim 15 wherein the program code for clustering the first nucleic acids includes:
program code for identifying a depth related to a set of first nucleic acids; and
program code for creating a cluster if the depth is below a predetermined value.

33. The computer program product of claim 15 wherein the program code for defining a distance includes:
program code for taking a difference between corresponding correlation matrix elements for each of the biological data of the first nucleic acids of a pair; and
program code for summing a function of each of the differences.

34. The computer program product of claim 15 wherein the distance is based on a similarity distance calculation.

35. The computer program product of claim 15, wherein the program code further includes:
program code for creating a complete list of all of the biological data linked to the target nucleic acid of the interactions;
program code for creating, for each first nucleic acid, a specific list of the biological data linked to the target nucleic acid with which that first nucleic acid interacts,
wherein the program code for associating, with a first nucleic acid, at least a portion of the biological data linked to the target nucleic acids with which that first nucleic acid interacts includes:
program code for comparing the specific list for the first nucleic acid to the complete list to determine the at least a portion of the biological data to associate with the first nucleic acid.

36. The method of claim 1, wherein a "0" value of a correlation matrix element indicates that specific biological data is not associated with a specific first nucleic acid and a "1" value of the correlation matrix element indicates that the specific biological data is associated with the specific first nucleic acid.

37. The method of claim 1, wherein a correlation matrix element indicates a degree that biological data is associated with each of the first nucleic acids.

* * * * *